US006544982B1

(12) United States Patent
Selnick et al.

(10) Patent No.: US 6,544,982 B1
(45) Date of Patent: Apr. 8, 2003

(54) THROMBIN RECEPTOR ANTAGONISTS

(75) Inventors: Harold G. Selnick, Ambler, PA (US); Philippe G. Nantermet, Lansdale, PA (US); James C. Barrow, Harleysville, PA (US); Roger M. Freidinger, Lansdale, PA (US); Thomas Connolly, Lansdale, PA (US)

(73) Assignee: Merck & Co., Inc., Rahway, NJ (US)

(*) Notice: Subject to any disclaimer, the term of this patent is extended or adjusted under 35 U.S.C. 154(b) by 0 days.

(21) Appl. No.: 09/698,811

(22) Filed: Oct. 27, 2000

Related U.S. Application Data

(60) Provisional application No. 60/162,586, filed on Oct. 29, 1999.

(51) Int. Cl.[7] .............. A61K 31/55; A61K 31/42; A61K 31/425; A61K 31/445; A61P 7/02; C07D 403/00; C07D 413/00; C07D 211/00; C07D 277/00

(52) U.S. Cl. .............. 514/217.1; 546/209; 548/146; 548/186; 548/245; 548/578

(58) Field of Search ................. 548/245, 146, 548/186, 578; 540/603, 480, 575; 546/184, 17, 19, 148, 187, 194, 199, 209; 514/210.2, 217.1, 218, 236.8, 253.1, 254.1, 254.04, 278, 307, 316, 318, 322, 326, 365, 380; 544/137, 364, 367

(56) References Cited

U.S. PATENT DOCUMENTS

| | | | |
|---|---|---|---|
| 5,446,131 A | 8/1995 | Maraganore | 530/236 |
| 5,457,177 A | 10/1995 | Veber et al. | 530/239 |
| 5,516,889 A | 5/1996 | Hollenberg et al. | 530/317 |
| 5,866,681 A | 2/1999 | Scarborough | 530/326 |
| 6,017,890 A | 1/2000 | Hoekstra et al. | 514/19 |
| 6,063,847 A | 5/2000 | Chackalamannil et al. | 524/297 |
| 6,156,732 A | 12/2000 | Hoekstra et al. | 514/18 |

FOREIGN PATENT DOCUMENTS

| | | | |
|---|---|---|---|
| DE | 32 37 149 | * | 4/1983 |
| DE | 19624282 A1 | * | 1/1998 |
| JP | 58-46077 | * | 3/1983 |
| JP | 62-59210 | * | 3/1987 |
| WO | WO 94/03479 | | 2/1994 |

OTHER PUBLICATIONS

G. Dannhardt et al., Hypertensive effects and structure-activity relationships of 5-omega-aminoalkylisozoles. Arzneim.-Forsch., 1993, 43 (4), 441–444.*

G. Dannhardt et al., Ring transformation of 2-phenacylideneimidazolidines into 5-(2-aminoethyl) aminoisoxazoles. Synthesis 1989, (1), 12–15.*

G. Dannhardt et al. 5-(beta-aminoethyl)aminoisoxazoles with hypertensive activity: Synthesis and screeining of derivatives with partially regid C-5 —, respectively. Arch. Pharm. (Weinheim, Ger.) 1990, 323 (9), 571–578.*

HCAPLUS printout for JP 62-59210, 1987.*

HCAPLUS printout for JP 58-46077, 1983.*

Bernatowicz, Michael, S. et al., "Development of Potent Thrombin Receptor Antagonict Peptides", *J. Med. Chem.*, pp. 4879–4887; 39: 1996.

Alexopoulos, K. et al., "A comparative SAR study of thrombin receptor derived non peptide mimetics: Importance of phenyl/guanidino proximity for activity", *Amino Acids*, pp. 211–220; 15: 1998.

* cited by examiner

*Primary Examiner*—Brenda Coleman
(74) *Attorney, Agent, or Firm*—Richard S. Parr; Melvin Winokur; Valerie J. Camara

(57) ABSTRACT

A thrombin receptor antagonist having the formula

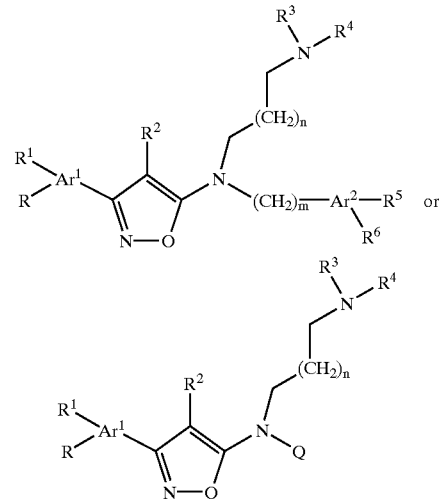

useful for inhibiting the aggregation of blood platelets. The compounds can be used in a method of acting upon a thrombin receptor which comprises administering a therapeutically effective but non-toxic amount of such compound to a mammal, preferably a human.

7 Claims, No Drawings

THROMBIN RECEPTOR ANTAGONISTS

CROSS-REFERENCE TO RELATED APPLICATIONS

This application claims the benefit of U.S. Provisional Application No. 60/162,586, filed Oct. 29, 1999.

BACKGROUND OF THE INVENTION

Thrombin is able to elicit many cellular responses (e.g. thrombotic, inflammatory, proliferative and atherosclerotic) that are mediated by proteolytic activation of a specific cell surface receptor known as tethered ligand receptor (Vu et al. (1991) *Cell* 64: 1057–1068; Rasmussen et al. (1991) *FEBS Lett* 288: 123–128; Zhong et al. (1992) *J. Biol. Chem.* 267: 16975–16979; Bahou et al. (1993) *J. Clin. Invest.* 91: 1405–1413; McNamara et al. (1993) *J. Clin. Invest.* 91: 94–98; Glembotski (1993) *J. Biol. Chem.* 268: 20646–20652; and Park et al. (1994) *Cardiovasc. Res.* 28: 1263–1268. The thrombin receptor has seven transmembrane-spanning domains and belongs to a family of G-protein coupled receptors (Vu et al. (1991) *Cell* 64: 1057–1068 and Schwartz (1994) *Current Opin. Biotechnol.* 5: 434–444). Activation of the receptor occurs by thrombin cleavage of an extracellular N-terminal domain. The new N-terminus through intramolecular interaction activates the receptor (Vu et al. (1991) *Cell* 64: 1057–1068; Coughlin (1993) *Thromb. Haemostas.* 70: 184–187; Van Obberghen-Schilling and Pouyssegur (1993) *Thromb. Haemostas.* 70: 163–167; Brass et al. (1994) *Ann. NY Acad. Sci.* 714: 1–12). Synthetic thrombin, receptor activating peptides comprising the 6–14 amino acids of the tethered ligand were found to activate platelets equally with thrombin itself and are considered to be full agonists (Vu et al. (1991) *Cell* 64: 1057–1068; Vassallo et al. (1992) *J. Biol. Chem.* 267: 6081–6085; Coller al. (1992) *Biochemistry* 31: 11713–11722; Chao et al. (1992) *Biochemistry* 31 6175–6178; Rasmussen et al. (1993) *J. Biol. Chem.* 268: 14322–14328). In contrast, only the first five amino acids (SFLLR) are required for activation of the platelet thrombin receptor (Scarborough et al. (1992) *J. Biol. Chem.* 267: 13146–13149; Hui et al. (1992) *Biochem. Biophys. Res. Commun.* 184: 790–796). Structure activity studies, NMR experiments and molecular modeling have determined the specific requirements for each amino acid in SFLLR (Matsoukas et al. (1997) *J. Prot. Chem.* 16: 113–131; Natarajan et al. (1995) *Int. J. Pept. Protein Res.* 45: 145–151).

SUMMARY OF THE INVENTION

Compounds of the invention are useful for inhibiting the aggregation of blood platelets. The above-mentioned compounds, which are thrombin receptor antagonists, can be used in a method of acting upon a thrombin receptor which comprises administering a therapeutically effective but non-toxic amount of such compound to a mammal, preferably a human. A pharmaceutical composition comprising a pharmaceutically acceptable carrier and, dispersed therein, an effective but non-toxic amount of active drug is another feature of this invention.

DETAILED DESCRIPTION OF THE INVENTION

The invention includes compounds having the formula

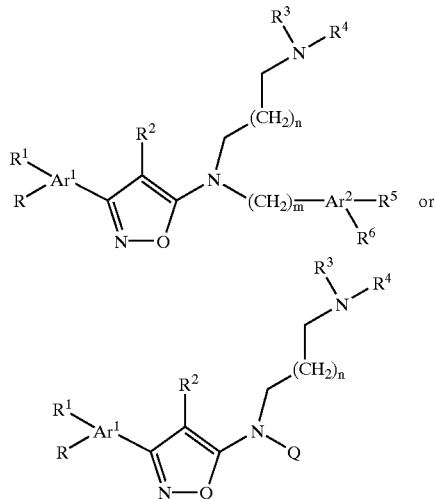

wherein
n is 0, 1, or 2;
m is 0, 1, or 2;
R is
  hydrogen,
  $C_{1-10}$ alkyl,
  $C_{1-10}$ alkoxy,
  aryl,
  halogen, or
  $CF_3$,
  $—OCH_3$,
  $SCH_3$,
  $SOCH_3$,
  $SO_2CH_3$,
  $NO_2$,
  CN, or
R, in combination with $R^1$, form a 5-membered heterocyclic ring having 1 or 2 heteroatoms;
$R^1$ is
  hydrogen,
  $C_{1-10}$ alkyl,
  $C_{1-10}$ alkoxy,
  aryl,
  halogen, or
  $CF_3$,
  $—OCH_3$,
  $SCH_3$,
  $SOCH_3$,
  $SO_2CH_3$,
  $NO_2$,
  CN, or
$R^1$, in combination with R, form a 5-membered heterocyclic ring having 1 or 2 heteroatoms;
$R^2$ is
  hydrogen,
  $C_{1-10}$ alkyl,
  $C_{1-10}$ alkoxy,
  halogen, or
  CN;
$R^3$ is
  hydrogen, $C_{1-10}$ alkyl,
$C_{3-7}$ alkanol,
$C_{2-10}$ alkenyl,
$C_{3-10}$ cycloalkyl,
$CH_2 \ C_{3-10}$ cycloalkyl,
$(CH_2)_2R^7$,
$CH_2R^7$,
CN,
$CH(CH_3)R^7$,
$R^7$,

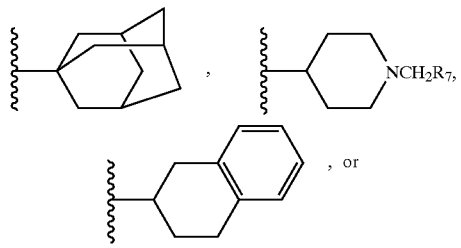, or $R^3$, in combination with $R^4$, forms a mono ring system selected from the group consisting of;
 a) a 4–8 membered saturated, partially saturated or unsaturated ring having 1 or 2 heteroatoms, unsubstituted or substituted with
  1) pyridine,
  2) COOEt,
  3) piperidine,
  4) $CONH_2$,
  5) $C_{1-4}$ alkyl, 6)
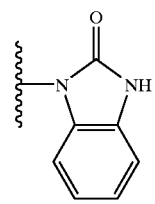

7)
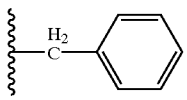

8)
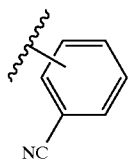

b)

c)
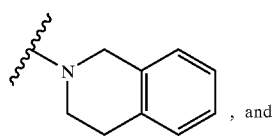, and d)
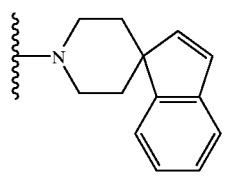

$R^4$ is
 hydrogen,
 $C_{1-10}$ alkyl,
 $C_{3-7}$ alkanol,
 $C_{2-10}$ alkenyl,
 $C_{3-10}$ cycloalkyl,
 $CH_2 \ C_{3-10}$ cycloalkyl,
 $(CH_2)_2R^7$,
 $CH_2R^7$,
 CN,
 $CH(CH_3)R^7$,
 $R^7$,

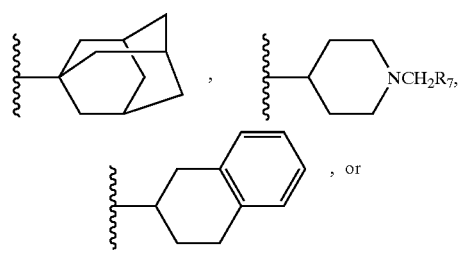, or $R^4$, in combination with $R^3$, forms a mono ring system selected from the group consisting of;
 a) a 4–8 membered saturated, partially saturated or unsaturated ring having 1 or 2 heteroatoms, unsubstituted or substituted with
  1) pyridine,
  2) COOEt,
  3) piperidine,
  4) $CONH_2$,
  5) $C_{1-4}$ alkyl, 6)
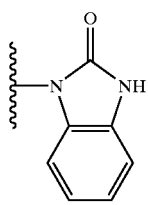

7)
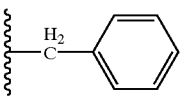

8)
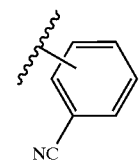

-continued b) 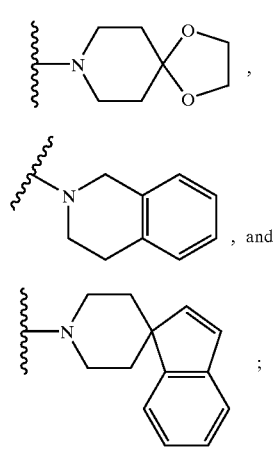

c)

d)

R⁵ is
   hydrogen,
   $C_{1-10}$ alkyl,
   $C_{1-10}$ alkoxy,
   CN,
   $OCF_3$, or
   —$O(CH_2)_{0-2}R^8$
   —$COOCH_2CH_3$, $NO_2$, $CF_3$,
   aryl, unsubstituted, monosubstituted or disubstituted with
      $OCH_3$,
      halogen,
      CN,
      $NO_2$,
      $CF_3$,
      $OCF_3$,
      $OCH_2Ph$,
      $OCH_2CH_2Ph$,
      COOEt,
      $C_{1-4}$ alkyl, or
      phenyl,

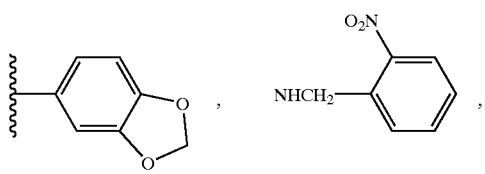

phenyloxy,
halogen, or
R⁵ and R⁶ form a 5 membered heterocyclic ring having 1 or 2 heteroatoms;
R⁶ is
   hydrogen,
   $C_{1-10}$ alkyl,
   $C_{1-10}$ alkoxy,
   CN,
   $OCF_3$, or
   —$O(CH_2)_{0-2}R^8$
   —$COOCH_2CH_3$, $NO_2$, $CF_3$,
   aryl, unsubstituted, monosubstituted or disubstituted with
      $OCH_3$,
      halogen;
      CN,
      $NO_2$,
      $CF_3$,
      $OCF_3$,
      $OCH_2Ph$,
      $OCH_2CH_2Ph$,
      COOEt,
      $C_{1-4}$ alkyl, or
      phenyl,

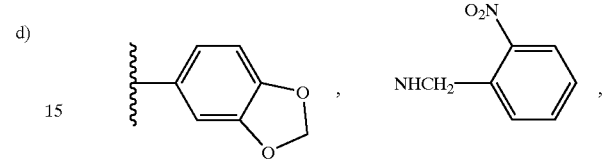

phenyloxy,
halogen, or
R⁶ and R⁵ form a 5 membered heterocyclic ring having 1 or 2 heteroatoms;
R⁷ is
   phenyl,
   $CH_2OCH_3$,
   $C_{3-6}$ cycloalkyl,

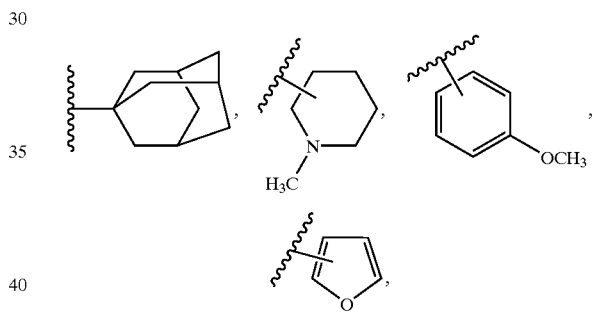

R⁸ is
   phenyl; and
Ar¹ and Ar² are independently aryl or heteroaryl; and
Q is —$C(O)C_{1-10}$ alkyl, —$C_{1-10}$ alkyl, or —$CH_2C_{3-10}$ cycloalkyl.

In a class of compounds of the invention, R² is hydrogen.

In a group of this class of compounds, R is hydrogen, F, Cl, I, $CH_3$, —$OCF_3$, $SCH_3$, $SOCH_3$, $SO_2CH_3$, CN, $NO_2$, or phenyl.

Specific embodiments of this group of compounds include

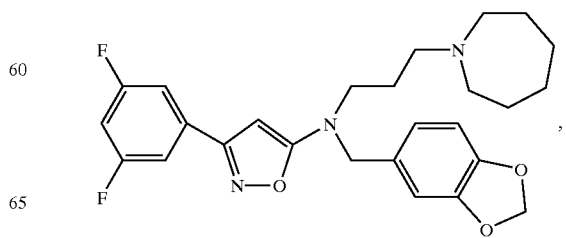

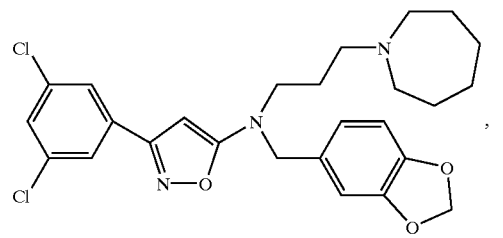,
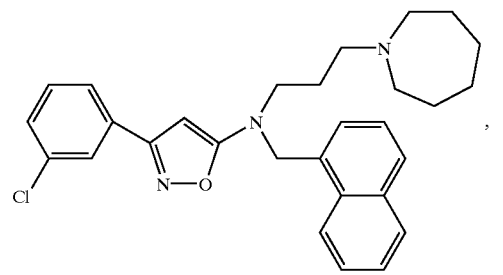,
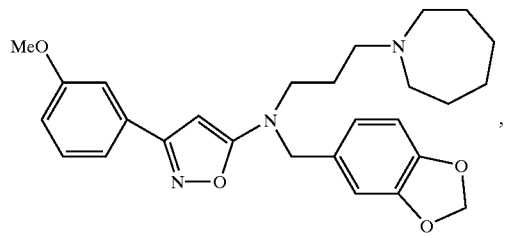,
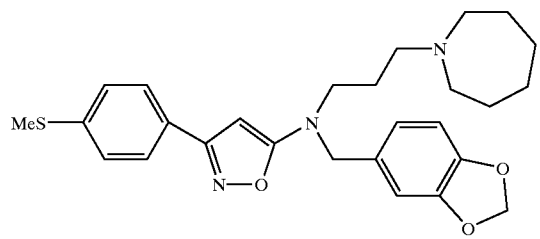,
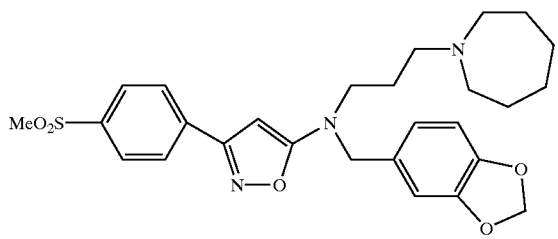,
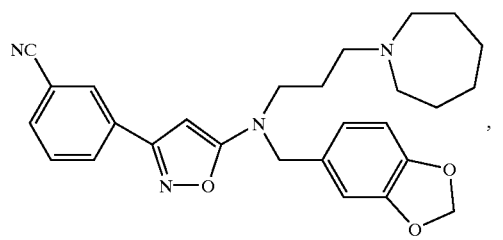,
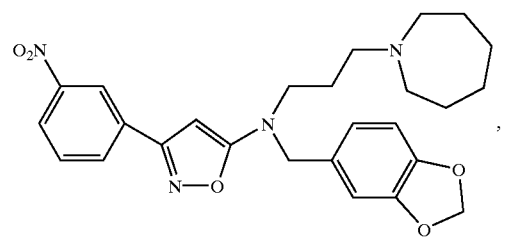,
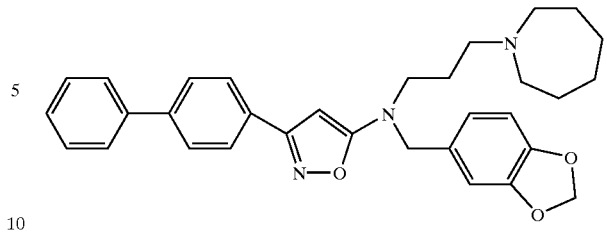,
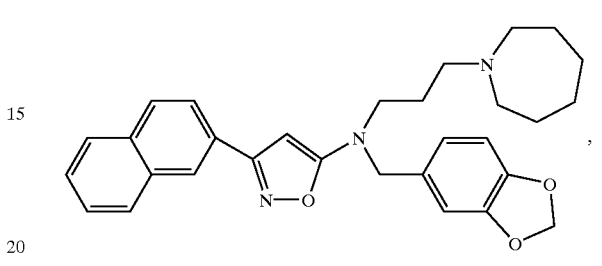,
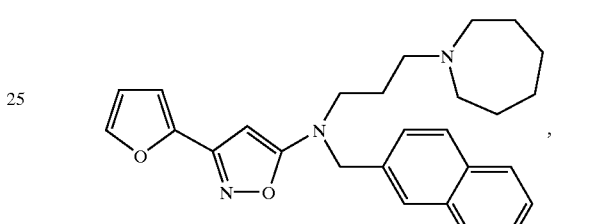,
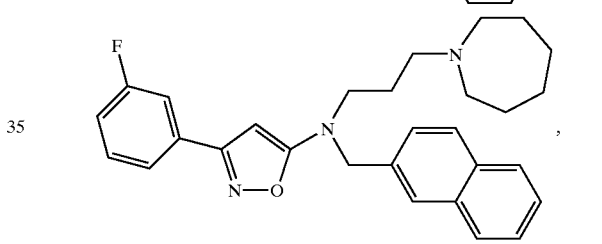,
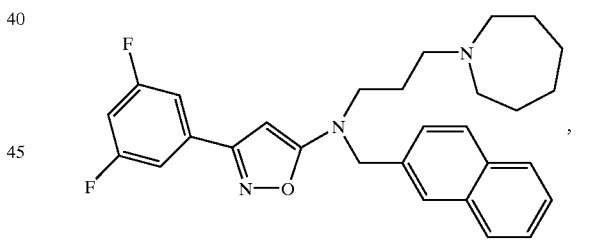,
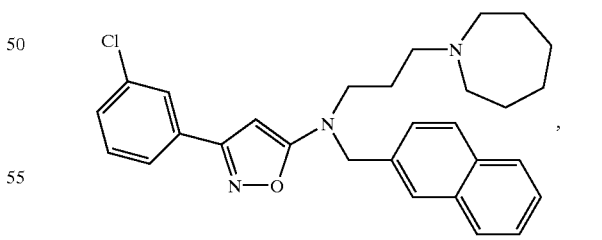,
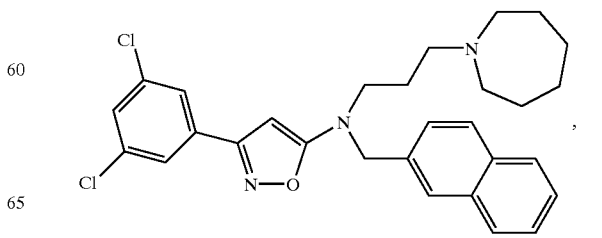,

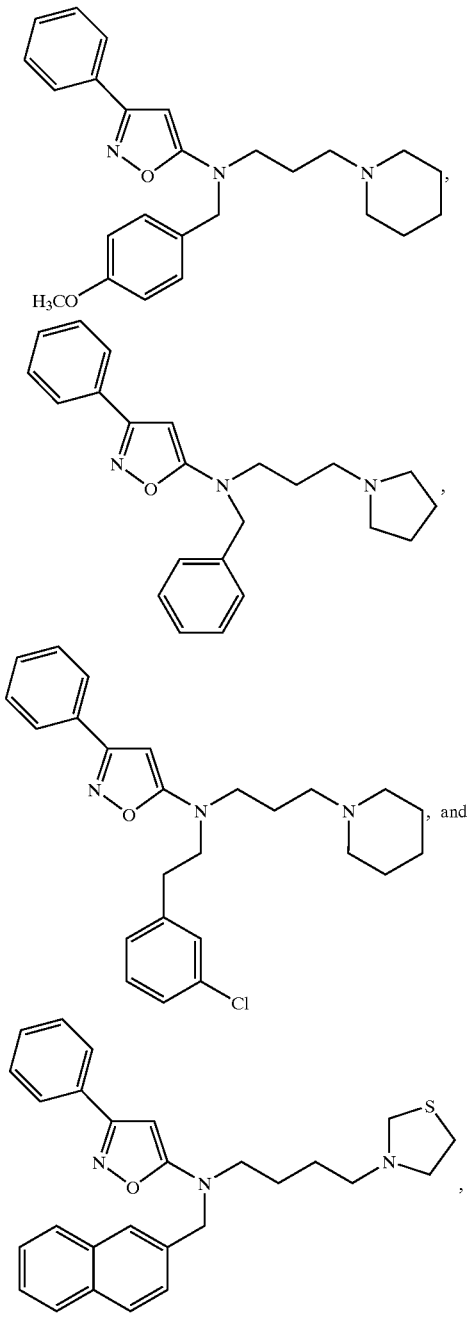

and pharmaceutically acceptable salts thereof.

The term "alkyl" means straight or branched alkane containing 1 to about 10 carbon atoms, e.g., methyl, ethyl, n-propyl, isopropyl, n-butyl, isobutyl, sec-butyl, tert-butyl, pentyl, iso-amyl, hexy, octyl radicals and the like.

The term "alkenyl" means straight or branched alkene containing 2 to about 10 carbon atoms, e.g., propylenyl, buten-1-yl, isobutenyl, pentenylen-1-yl, 2,2-methylbuten-1-yl, 3-methylbuten-1-yl, hexen-1-yl, hepten-1-yl, and octen-1-yl radicals and the like.

The term, "alkynyl" means straight or branched alkyne containing 2 to about 10 carbon atoms, e.g., ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like.

The term "alkoxy" means straight or branched alkane containing 1 to about 10 carbon atoms bonded to an oxygen atom, which is attached to the indicated substituted atom, e.g., methoxy, ethoxy, n-propoxy, isopropoxy, n-butoxy; isobutoxy, sec-butoxy, tert-butoxy, pentyloxy, radicals and the like.

The term "halogen" includes fluorine, chlorine, iodine and bromine.

The term "oxy" means an oxygen (O) atom.

The term "thio" means a sulfur (S) atom.

The term "aryl" means a partially saturated or fully saturated 6–14 membered ring system such as for example, phenyl, naphthyl or anthracyl. The term "Ph", which appears in certain chemical formulas in the specification and claims, represents phenyl.

The term "heteroaryl means a partially or fully saturated 5 or 6-membered ring system having 1 or 2 heteroatoms selected from the group consisting of N, O, and S, for example, pyridine, furan, pyrazine, pyrimidine, thiophene, pyran, pyrrole, thiazole, isoxazole, triazine, and furazan.

Under standard nonmenclature used throughout this disclosure, the terminal portion of the designated side chain is described first followed by the adjacent functionality toward the point of attachment. For example, a methylene substituted with ethylcarbonylamino is equivalent to

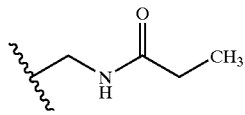

The term "cycloalkyl" means straight or branched alkane containing 3 to about 10 carbon atoms, e.g., cyclopropyl, cyclobutyl, cyclopentyl, cyclohexy, cycloheptyl, cyclooctyl radicals and the like.

The term "heterocyclic" or "heterocycle" means a cyclic ring system containing 3 to about 10 atoms, at least one of which is a heteroatom selected from the group conistsing of N, O and S. With "n" representing the total number of ring atoms, the maximum number of heteroatoms present in the ring is equal to the number represented by one-half of "n" when n is 4, 6, 8, or 10, and one-half of "n−1" when n is 3, 5, 7, or 9. Examples of heterocyclic rings include piperidine, dioxane, tetrahydrofuran, imidazolidine, oxathiolane, and, octahydroazocine.

Compounds of the present invention may be chiral; included within the scope of the present invention are racemic mixtures and separated enantiomers of the general formula. Furthermore, all diastereomers, including E, Z isomers, of the general formula are included in the present scope. Furthermore, hydrates as well as anhydrous compositions and polymorphs of the general formula are within the present invention. Thus, the term "active drug" includes a compound of the invention and its salts, racemic mixtures or separated enantiomers, hydrates or anhydrous forms, polymorphs, and pharmaceutically acceptable salts.

The term "pharmaceutically acceptable salts" shall mean non-toxic salts of the compounds of this invention which are generally prepared by reacting the free base with a suitable organic or inorganic acid. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, valerate.

Prodrugs, such as ester derivatives of active drug are compound derivatives which, when absorbed into the bloodstream of a warm-blooded animal, cleave in such a manner as to release the drug form and permit the drug to afford improved therapeutic efficacy.

The term "pharmaceutically effective amount" shall mean that amount of a drug or pharmaceutical agent that will elicit the biological or medical response of a tissue, system or animal that is being sought by a researcher or clinician. The term "anti-coagulant" shall include heparin, and warfarin. The term "thrombolytic agent" shall include agents such as streptokinase and tissue plasminogen activator. The term "platelet anti-aggregation agent" shall include agents such as aspirin and dipyridamole.

In the schemes and examples below, various reagent symbols have the following meanings:

| | |
|---|---|
| BOC (or Boc): | t-butyloxycarbonyl |
| Pd-C: | Palladium on activated carbon catalyst |
| DMF: | Dimethylformamide |
| DMSO: | Dimethylsulfoxide |
| CBZ: | Carbobenzyloxy |
| $CH_2Cl_2$: | Methylene chloride |
| $CHCl_3$: | chloroform |
| EtOH: | ethanol |
| MeOH: | methanol |
| EtOAc: | ethyl acetate |
| HOAc: | acetic acid |
| BOP: | Benzotriazol-1-yloxytris(dimethylamino)phosphonium, hexafluorophosphate |
| EDC: | 1-(3-Dimethylaminopropyl)-3-ethylcarbodiimide hydrochloride |
| Oxone: | potassium peroxymonosulfate |
| LDA: | Lithium diisopropylamide |

Active drug can be administered in such oral forms as tablets, capsules (each of which includes sustained release or timed release formulations), pills, powders, granules, elixirs, tinctures, suspensions, syrups, and emulsions. Likewise, it may be administered in intravenous (bolus or infusion), intraperitoneal, subcutaneous, or intramusculsar form, all using forms well known to those of ordinary skill in the pharmaceutical arts. An effective but non-toxic amount of active drug can be employed as an anti-aggregation agent.

Active drug may be administered to patients where prevention of thrombosis by inhibiting binding of thrombin to the thrombin receptor is desired. It is useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. Active drug may be administered to these surgical patients to prevent the formation of thrombi and thromboemboli.

Other applications of active drug include prevention of platelet thrombosis, thromboembolism and reocclusion during and after thrombolytic therapy and prevention of platelet thrombosis, thromboembolism and reocclusion after angioplasty or coronary artery bypass procedures. It may also be used to prevent myocardial infarction.

The dosage regimen utilizing active drug is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of active drug when used for the indicated effects, will range between about 0.005 mg per kg of body weight per day (mg/kg/day) to about 50 mg/kg/day and preferably 0.005–20 mg/kg/day and most preferably 0.005–10 mg/kg/day. For example, a typical 90 kg patient would receive oral dosages ranging between about 0.45 mg/day and about 4.5 g/day, most preferably between about 1.0 mg/day and 1.0 g/day. Suitable pharmaceutical oral compositions such as tablets or capsules may contain 1–500 mg, for example, 1 mg, 10 mg, 100 mg, 200 mg and 500 mg. Intravenously, the most preferred doses will range from about 0.5 to about 5 mg/kg/minute during a constant rate infusion. Active drug may be administered in one or divided doses of two, three, or four times daily. Furthermore, active drug can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather that intermittent throughout the dosage regime.

In the methods of the present invention, the active drug can form the active ingredient, and is typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, When desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The active drug can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Active drug may also be delivered by the use of monoclonal antibodies as individual carriers to which the compound molecules are coupled. Active drug may also be coupled with soluble polymers as targetable drug carriers. Such polymers can include polyvinyl-pyrrolidone, pyran copolymer, polyhydroxy-propyl-methacrylamide-phenol, polyhydroxy-ethyl-aspartamide-phenol, or polyethyleneoxide-polylysine substituted with palmitoyl residues. Furthermore, active drug may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

Active drug can also be co-administered with the usual doses of suitable anticoagulation agents, such as heparin or warfarin (typically given in tablet doses between 1 and 20 mg daily during administration of the active drug), or thrombolytic agents such as tissue plasminogen activator (typically given in i.v. doses of between 20 and 150 mg over two hour period prior to or during administration of the active drug), to achieve beneficial effects in the treatment of various vascular pathologies. Such co-administration also includes administration if the active drug with doses of anticoagulant agents or thrombolyric agents less than the usual doses of those agents.

Compounds of the invention were prepared according to the following general schemes, including the specific procedures described in the following examples. Those skilled in the art will readily understand that known variations of the conditions and processes of the following preparative procedures can be used to prepare these compound. All temperatures are degrees Celsius unless otherwise noted.

Scheme 1

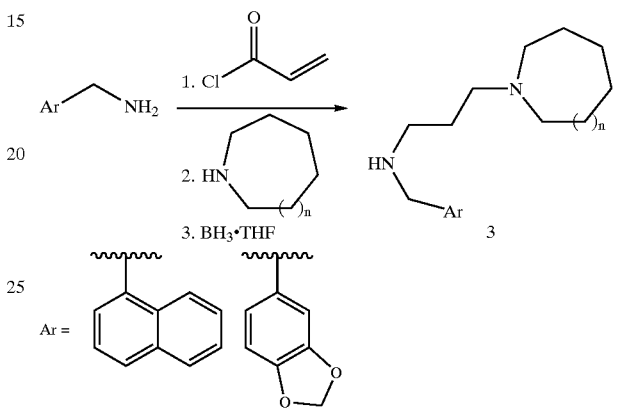

Scheme 2

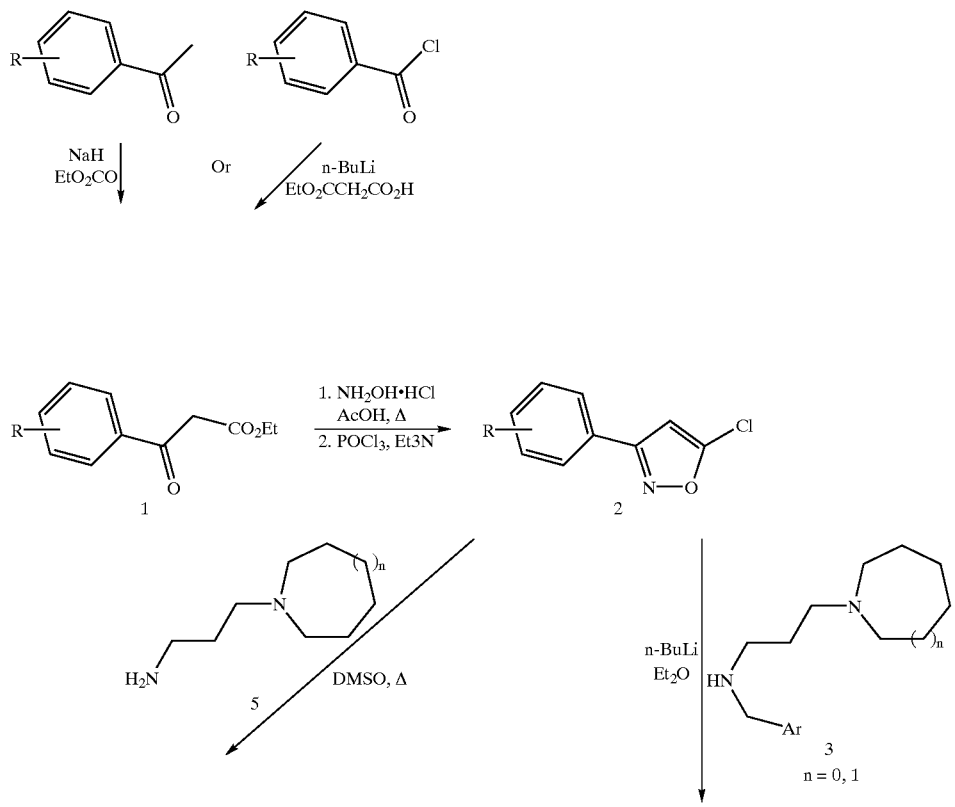

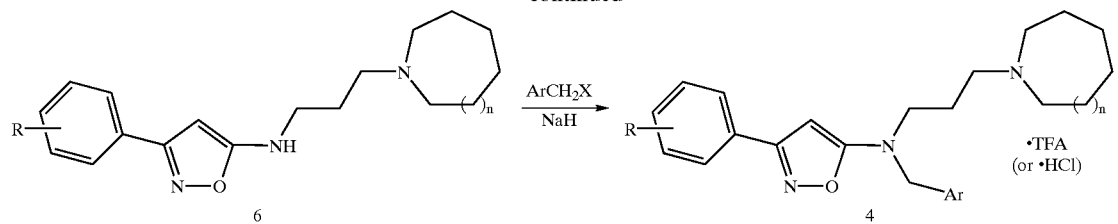
Scheme 1
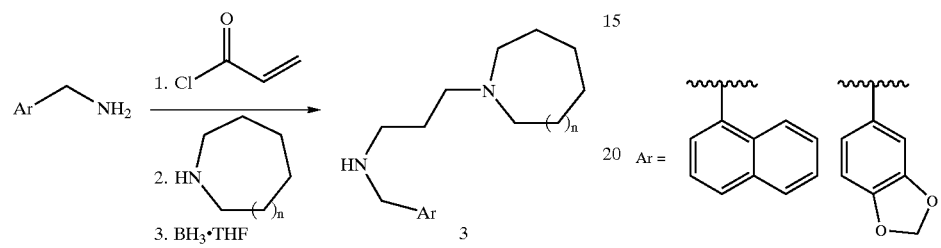
Scheme 2
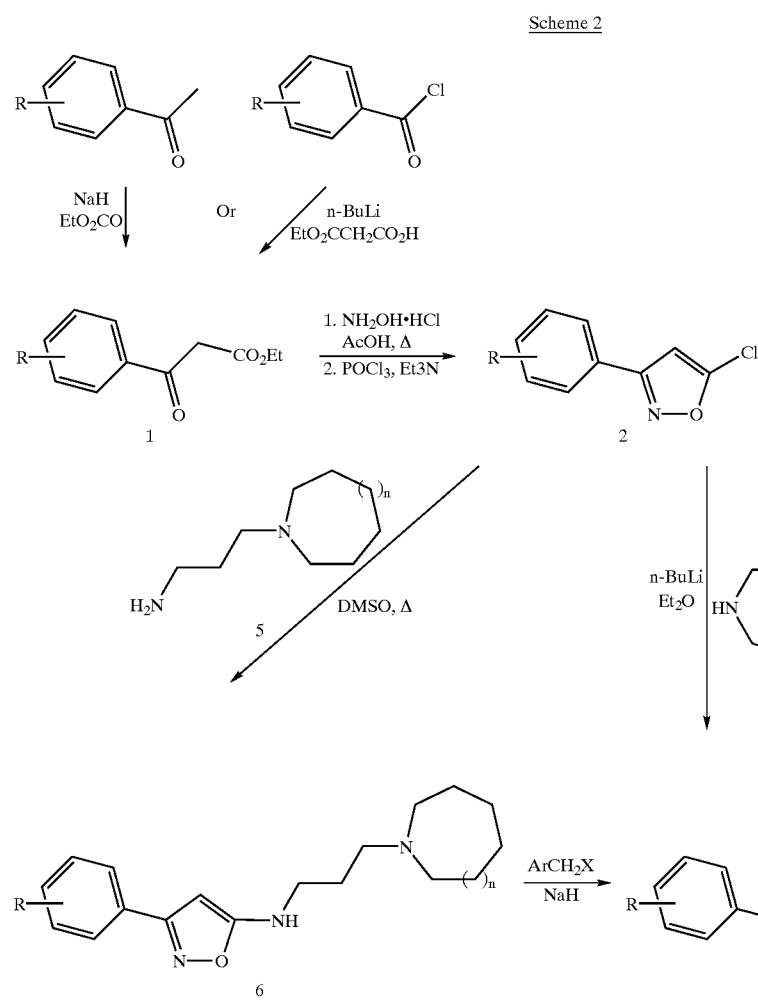

Scheme 3

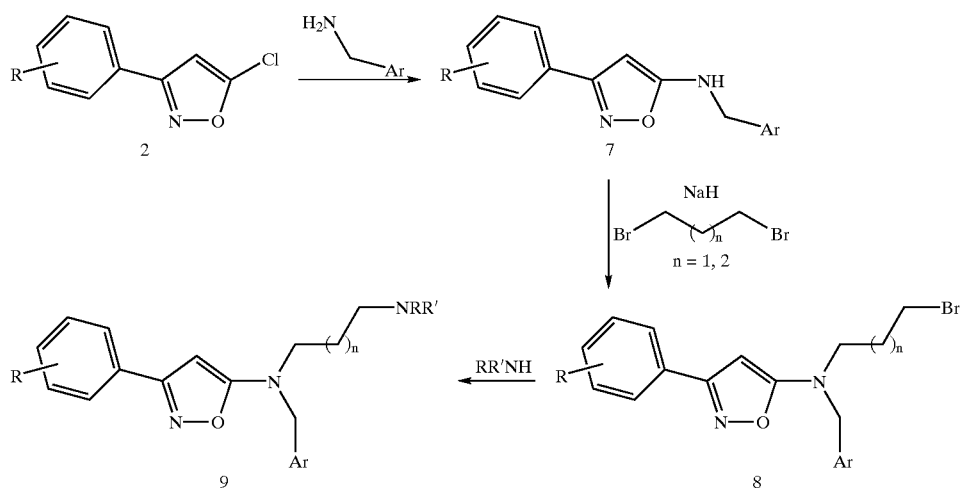

Scheme 4

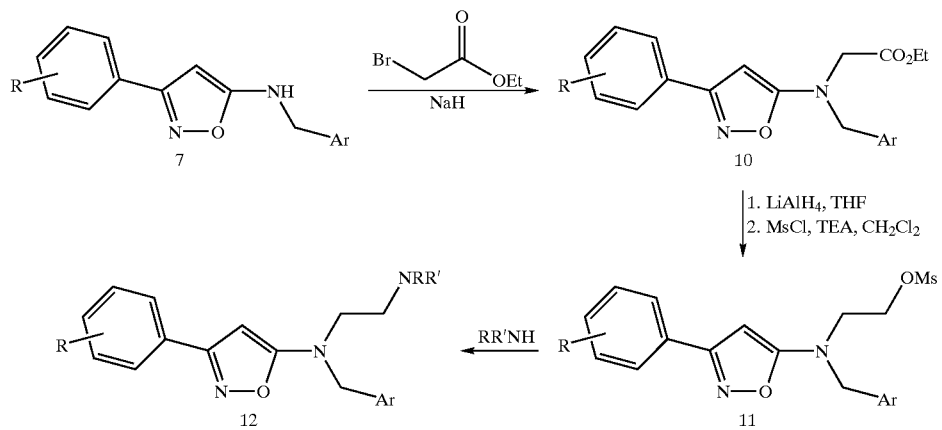

The proposed 5-amino-isoxazoles bearing substituted phenyl groups at the 3 position can be prepared according to the following general methods.

Substituted acetophenones can be reacted with diethyl carbonate in the presence of sodium hydride to provide β-keto esters of type 1. β-keto esters are aslo available from the condensation of ethyl monomalonate ester on benzoyl chlorides in the presence of n-BuLi. Reaction of such β-keto esters with hydroxylamine hydrochloride in refluxing acetic acid provides the corresponding isoxazolones after solvent evaporation. These are chlorinated without further purification, with phosphorus oxychloride to provide 5-chloro-isoxazoles of type 2. Amines of type 3 can be lithiated in the presence of nBuLi and reacted with the previous 5-chloro-isoxazoles to provide the compounds of interest 4. Alternatively, reaction of amines 5 with chloroisoxazoles 2 provides amines of type 6 which can be alkylated with benzyl halides, in the presence of NaH, to give the compounds of interest 4. Amines of type 3 can be prepared from benzyl amines by acylation with acryloyl chloride, Michael addition with piperidine or azepine, and borane reduction. Compounds of the present invention are also prepared according to Schemes 3 and 4.

EXAMPLE 1

3,4-Methylenedioxybenzyl-(3-azepin-1-yl-propyl)-amine

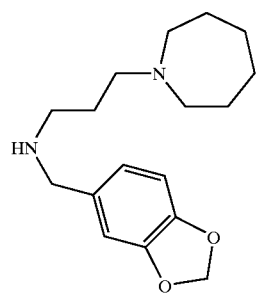

Step A: 3,4-Methylenedioxybenzyl-(3-azepin-1-yl)-propionamide

To a stirring solution of piperonyl amine in (15.1 g, 100 mmole) and triethyl amine (10.5 g, 100 mmole) in methylene chloride ( 300 mL) at 0° C. was added acryloyl chloride (9.1 g, 100 mmole) dropwise over 5 minutes. The reacion was concentrated at reduced pressure and the residue diluted with ethyl acetate (200 mL). The solution was washed with saturated sodium bicarbonate (200 mL), dried over sodium sulfate, and concentrated in vacuo. The residue was dissolved in DMF (20 mL) and methylene chloride (50 mL) and then hexamethylene imine was added and the reaction stirred overnight at room temperature. The reaction mixture is diluted with ethyl acetate, washed with water and brine, dried over sodium sulfate, and concentrated in vacuo to give 3,4-methylenedioxybenzyl-(3-azepin-1-yl-propionyl)-amide (20 g).

$^1$H NMR (CDCl$_3$, 300 MHz) δ9.2 (br s, 1H); 6.8 (s, 1H); 6.75 (s, 2H); 5.9 (s, 2H); 4.3 (d, J=5.5 Hz, 2H); 2.7–2.6 (m, 4H); 2.6–2.5 (m, 4H); 2.4–2.3 (m, 2H); 1.7–1.4 (m, 12H).

Step B: 3,4-Methylenedioxybenzyl-(3-azepin-1-yl-propyl)-amine 3,4-methylenedioxybenzyl-(3-azepin-1-yl-propionyl)-amide (20 g, 69 mmole) was dissolved in THF and treated with a solution of Borane/THF (1M, 138 mL, 138 mmole) and heated to reflux for 5 hours. Added another 60 mL borane/THF and heated for 4 hours. The reaction was cooled to room temperature and quenched by the careful addition of ethanol (20 mL) and then 6 N HCl (100 mL). The mixture was concentrated at reduced pressure and redissolved in 6N HCl (200 mL) and methanol (100 mL) and heated gently for 15 minutes. After cooling the solution was extracted once with ether (100 mL) and then basified to pH 12 with aqueous sodium hydroxide. This was then extracted with ethyl acetate (3×200 mL) and the combined ethyl acetate extracts were dried over anhydrous sodium sulfate, filtered and concentrated at reduced pressure to give 15 g of the product.
$^1$H NMR (CDCl$_3$, 300 MHz) δ6.82 (s, 1H); 6.76 (s, 2H); 5.95 (s, 2H); 3.7 (s, 2H); 2.7–2.46 (m, 8H); 1.7–1.5 (m, 10H).

EXAMPLE 2

1-Naphthylmethyl-(3-azepin-1-yl-propyl)amine

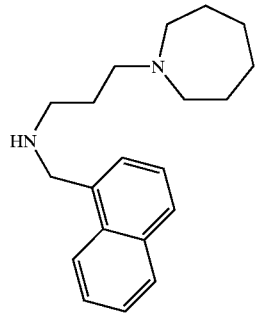

Prepared in a manner substantially the same as that described for EXAMPLE 1 except substituting 1-aminomethylnaphlalene for piperonyl amine in Step A.

$^1$H NMR (CDCl$_3$, 300 MHz) δ6.82 (s, 1H); 6.76 (s, 2H); 5.95 (s, 2H); 3.7 (s, 2H); 2.7–2.46 (m, 8H); 1.7–1.5(m, 10H).

EXAMPLE 3

3,4-Methylenedioxybenzyl-[3-(3,5-difluorophenyl)-isoxazol-5-yl]-(-3-azepin-1-yl-propyl)-amine hydrochloride

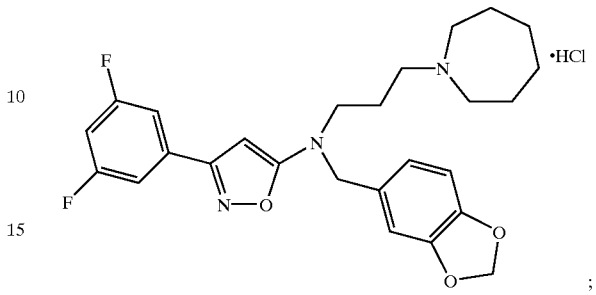

Step A. 3,5-difluorobenzoylacetate

To a suspension of 3,5-difuroacetophenone (1.5 g, 9.6 mmol) in diethyl carbonate (23 ml) cooled to 0° C. is added NaH (698 mg, 19.2 mmol, 60% dispersion in oil) by portions. The resulting reaction mixture is stirred at 80° C. for 2 hrs. After cooling to 25° C., the reaction mixture is poured into cold water/acetic acid (50 ml/1.7 ml) and extracted with diethyl ether twice. The combined organic layer is dried over sodium sulfate, concentrated in vacuo and the crude product is purified by flash chromatography (silica gel, dry loading, hexane to 5% diethyl ether in hexane) to provide ethyl 3,5-difluorobenzoylacetate (1.87 g, 85%), as a yellow solid.
$^1$H NMR (CDCl$_3$, 300 Mhz) (1.9:1 keto:enol mixture): δ12.55 (s, 0.34 H); 7.55–7.40 (m, 1.32 H); 7.35–7.20 (m, 0.68 H); 7.15–7.00(m, 0.66 H); 6.95–6.85 (m, 0.34 H); 5.63 (s, 0.34 H); 4.35–4.15 (m, 2 H); 3.93 (s, 1.32 H); 1.40–1.20 (m, 3H).

Step B. Give 3-(3,5-difluorophenyl)-5-chloroisoxazole

A mixture of ethyl 3,5-difluorobenzoylacetate (1.87 g, 8.19 mmol) and hydroxylamine hydrochloride (626 mg, 9.01 mmol) in acetic acid (24 ml) is stirred at reflux for 1 hr. The crude reaction mixture is concentrated in vacuo and azeotroped with toluene twice. The crude material is suspended in phosphorus oxychloride (37 ml) and triethyl amine (2.37 ml, 17.1 mmol) is added slowly. The reaction mixture is stirred at reflux for 2 days, concentrated in vacuo and azeotroped with toluene 3 times. The residue is dissolved in dichloromethane and passed on a plug of silica gel (elution with dichloromethane. After concentration in vacuo, the crude material is purified by flash chromatography (silica gel, dry loading, 5% diethyl ether in hexane) to give 3-(3, 5-difluorophenyl)-5-chloroisoxazole (600 mg, 35%) as an off-white solid.
$^1$H NMR (CDCl$_3$, 300 MHz): δ7.34–7.24 (m, 2 H); 6.98–6.88 (m, 1 H); 6.46,(s, 1 H).

Step C. 3,4-Methylenedioxybenzyl-[3-(3,5-difluorophenyl)-isoxazol-5-yl]-(3-azepin-1-yl-propyl)-amine hydrochloride To a solution of 3,4-methylenedioxybenzyl-(3-azepin-1-yl-propyl)amine in diethyl ether (26.7 ml of a 0.12 M solution in diethyl ether, 3.22 mmol) cooled to 0° C. is slowly added n-BuLi (1.51 ml of a 1.6M solution in hexane, 2.41 mmol). The resulting mixture is stirred at 0° C. for 10 min and 3-(3,5-difluorophenyl)-5-chloroisoxazole (347 mg, 1.61 mmol) is added at once. After stirring at 0° C. for 30 min, the reaction mixture is dilute with ethyl acetate, washed with water andbrine, dried over sodium sulfate, and concentrated in vacuo. The crude material is purified by flash chromatography (silica gel, 3% methanol containing 10% $NH_4OH$ in dichloromethane) to give the free base of the title compound as an oil. The free base is dissolved in dichloromethane (10 ml) and treated with 1 N HCl in diethyl ether (4 ml, 4 mmol) to provide after concentration in vacuo, 3,4-methylenedioxybenzyl-[3-(3,5-difluorophenyl)-isoxazol-5-yl]-(3-azepin-1-yl-propyl)-amine hydrochloride (513 mg, 63%) as a pale yellow foam.

MS (FAB) M+1=470.1.

$^1$H NMR ($CDCl_3$, 400 Mhz): δ12.25 (br s, 1 H); 7.30–7.22 (m, 2 H); 6.92–6.84 (m, 1 H); 6.82–6.76 (m, 3 H); 5.96 (s, 2 H); 5.34 (s, 1 H); 4.50 (s, 2 H); 3.56–3.44 (m, 4 H); 3.00–2.90 (m, 2 H); 2.90–2.75 (m, 2 H); 2.35–2.24 (m, 2 H); 2.22–2.06 (m, 2 H);1.92–1.74 (m, 4 H); 1.68–1.54 (m, 2H).

CHN analysis calc. for $C_{26}H_{29}F_2N_3O_3 \cdot HCl \cdot 0.55\ H_2O$:C, 60.53; H, 6.08; N, 8.15; found: C, 60.58; H,8.82; N, 7.88.

EXAMPLE 4

3,4-Methylenedioxybenzyl-[3-(3,5-difluorophenyl)-isoxazol-5-yl](3-azepin-1-yl-propyl)-amine TFA salt

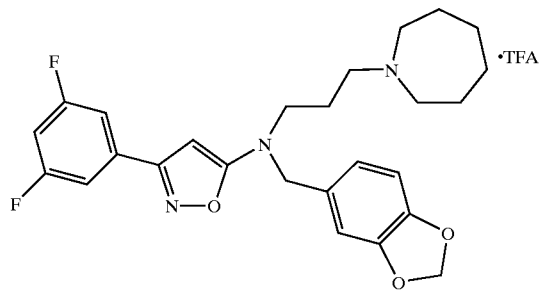

To a solution of 3,4-methylenedioxybenzyl-(3-azepin-1-yl-propyl)-amine in diethyl ether (0.75 ml of a 0.12 M solution in diethyl ether, 0.09 mmol) cooled to 0° C. is slowly added n-BuLi (45 ul of a 1.6M solution inhexane, 0.072 mmol). The resulting mixture is allowed to stand at 0° C. for 5 min and 3-(3,5-difluorophenyl)-5-chloroisoxazole (12.9 mg, 0.06 mmol) is added atonce. After standing at 0° C. for 30 min, the solvent is evaporated under a stream of argon. The residue is dissolved in DMF (0.4 ml) and water (0.04 ml) and purified by preparative HPLC (20×50 mm C18, 0.1%TFA ACN/water gradient) to provide after solvent evaporation: 3,4-methylenedioxybenzyl-[3-(3,5-difluorophenyl)-isoxazol-5-yl]-(3-azepin-1-yl-propyl)-amine TFA salt (9.2 mg, 33%) as film.

HRMS (ES): M+1 calc. for $C_{26}H_{29}F_2N_3O_3$: 470.2250 found: 470.2264.

$^1$H NMR ($CDCl_3$, 300 Mhz): δ12.05 (br s, 1 H); 7.35–7.15 (m, 2 H); 6.95–6.80 (m, 1 H); 6.80–6.70 (m, 3 H); 5.96 (s, 2 H); 5.29 (s, 1 H); 4.42 (s, 2 H); 3.62–3.38 (m, 4 H); 3.10–2.95 (m, 2 H); 2.93–2.80 (m, 2 H); 2.15–1.85 (m, 4 H); 2.9–1. (m, 6 H).

EXAMPLE 5

1-Naphthylmethyl-[3-(3,5-difluorophenyl)-isoxazol-5-yl]-(3-azepin-1-yl-propyl)amine TFA salt

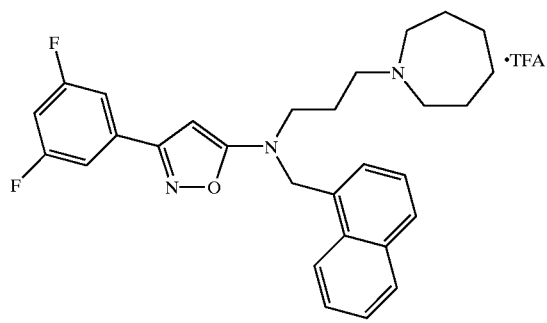

The title compound is prepared using a similar procedure as described for the preparation of 3,4-methylenedioxybenzyl-[3-(3,5-difluorophenyl)-isoxazol-5-yl]-(3-azepin-1-yl-propyl)-amine TFA salt (example 4) while substituting 1-Naphthylmethyl-(3-azepin-1-yl-propyl)-amine for 3,4-methylenedioxybenzyl-(3-azepin-1-yl-propyl)-amine.

HRMS (ES): M+1 calc. for $C_{29}H_{31}F_2N_3O$: 476.2508, found: 476.2509.

EXAMPLE 6

3,4-Methylenedioxybenyl-[3-(3,5-dichlorophenyl)-isoxazol-5-yl]-(3-azepin-1-yl-propyl)amine hydrochloride

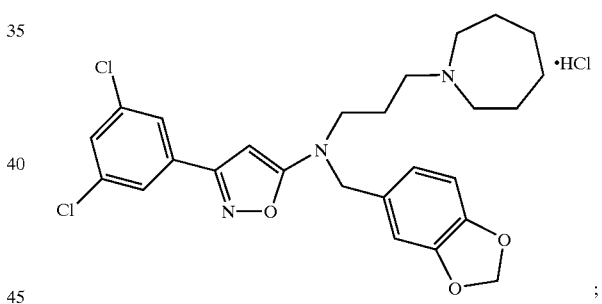

Step A. ethyl-3,5-dichlorobenzoylacetate

To a solution of monoethyl malonate (5.79 g, 43.8 mmol) in THF (100 ml) is added a catalyitc amount of 2,2'-bipyridine and the reaction mixture is cooled to –20° C. n-BuLi (54.8 ml, 1.6 M, 87.65 mmol) is slowly added while maintaining the reaction temperature between –20° C. and 0° C. At the end of addition the heterogeneous reaction mixture remains pink and is stirred at –5° C. for 10 min. The reaction mixture is cooled to –78° C. and 3,5-dichlorobenzoyl chloride (5.1 g, 24.3 mmol) in THF (20 ml) is added dropwise. The reaction mixture is allowed to warm to –35° C., quenched with 1N HCl (50 ml), and allowed to warm to room temperature. The reaction mixture is extracted with diethyl ether which is washed with brine, dried over magnesium sulfate and concentrated in vacuo, to provide, after purification by flash chromatography (silica gel, hexane to 5% diethyl ether in hexane), ethyl-3,5-dichlorobenzoylacetate (4.86 g, 76%), as a pale orange oil.

$^1$H NMR ($CDCl_3$, 300 MHz) (1:1 keto:enol mixture): δ12.50 (s, 0.5 H); 7.80 (d, 1H, 2 Hz); ); 7.64 (d, 1H, 2 Hz);

7.58 (t, 0.5H, 2 Hz); ); 7.44 (t, 0.5H, 2 Hz); 5.64 (s, 0.5H); 4.35–4.15 (m, 2H); 3.94 (s, 1H); 1.40–1.22 (m, 3H).

Following a similar protocol as described in example 3, ethyl 3,5-dichlorobenzoylacetate is converted to 3,4-methylenedioxybenzyl-[3-(3,5-dichlorophenyl)-isoxazol-5-yl]-(3-azepin-1-yl-propyl)-amine hydrochloride, obtained as a pale yellow foam.

HRMS (ES): M+1 calc. for $C_{26}H_{29}Cl_2N_3O_3$: 502.1659, found: 502.1681.

CHN analysis calc. for $C_{26}H_{29}Cl_2N_3O_3 \cdot HCl \cdot 0.55 H_2O \cdot 0.35 CH_2Cl_2$: C, 55.48; H, 5.46; N, 7.37; found: C, 55.44; H, 5.38; N, 7.35.

The following EXAMPLEs 7–60 are all prepared following protocols similar to those described in examples 1–6

EXAMPLE 7

3,4-Methylenedioxybenzyl-[3-(2-chlorophenyl)-isoxazol-5-yl]-(3-azepin-1-yl-propyl)amine TFA salt

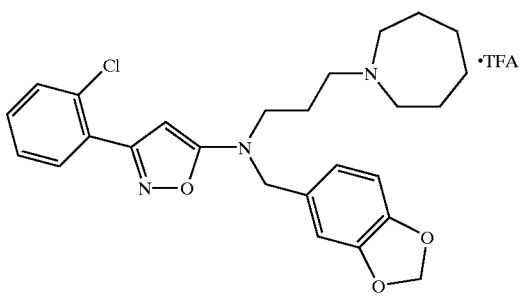

HRMS (ES): M+1 calc. for $C_{26}H_{30}ClN_3O_3$: 468.2048, found: 468.2054.

EXAMPLE 8

1-Naphthylmethyl-[3-(2-chlorophenyl)-isoxazol-5-yl]-(3-azepin-1-yl-propyl)-amine TFA salt

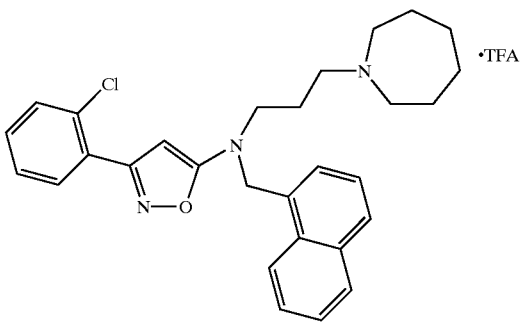

HRMS (ES): M+1 calc. for $C_{29}H_{32}ClN_3O$: 474.2307, found: 474.2307.

EXAMPLE 9

3,4-Methylenedioxybenzyl-[3-(3-chlorophenyl)-isoxazol-5-yl]-(3-azepin-1-yl-propyl)-amine TFA salt

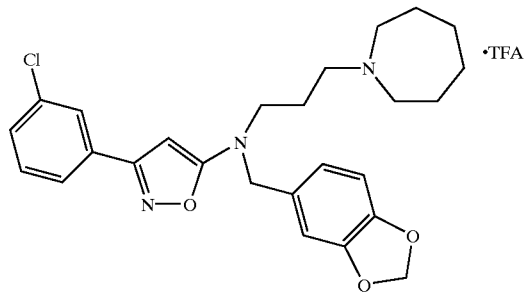

HRMS (ES): M+1 calc. for $C_{26}H_{30}ClN_3O_3$: 468.2048, found: 468.2055.

EXAMPLE 10

1-Naphtylmethyl-[3-(3-chlorophenyl)-isoxazol-5-yl]-(3-azepin-1-yl-propyl)-amine TFA salt

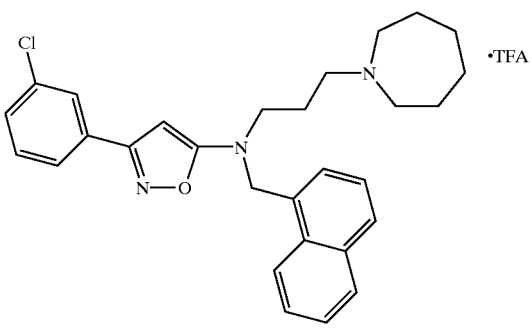

HRMS (ES): M+1 calc. for $C_{29}H_{32}ClN_3O$: 474.2307, found: 474.2316.

EXAMPLE 11

3,4-Methylenedioxybenzyl-[3-(4-chlorophenyl)-isoxazol-5-yl]-(3-azepin-1-yl-propyl)-amine TFA salt

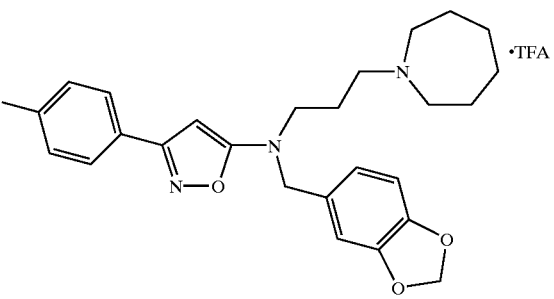

HRMS (ES): M+1 calc. for $C_{26}H_{30}ClN_3O_3$: 468.2048, found: 468.2053.

EXAMPLE 12

1-Naphthylmethyl-[3-(4-chlorophenyl)-isoxazol-5-yl]-(3-azepin-1-yl-propyl)-amine TFA salt

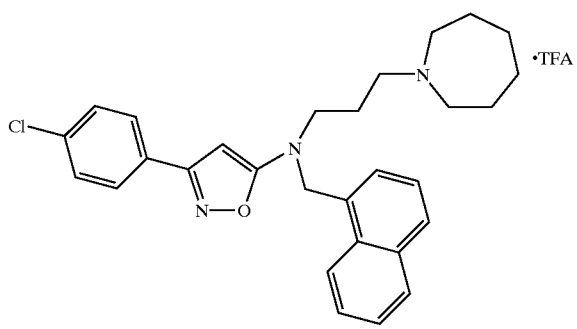

HRMS (ES): M+1 calc. for $C_{29}H_{32}ClN_3O$: 474.2307, found: 474.2316.

EXAMPLE 13

3,4-Methylenedioxybenzyl-[3-(3-fluorophenyl)-isoxazol-5-yl]-(3-azepin-1-yl-propyl)-amine TFA salt

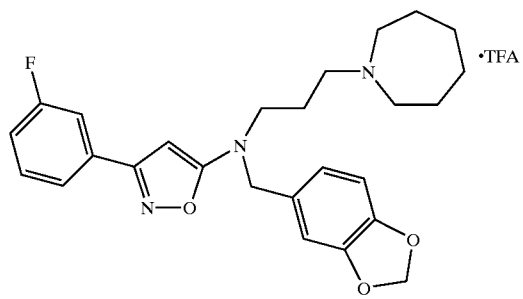

HRMS (ES): M+1 calc. for $C_{26}H_{30}FN_3O_3$: 452.2344, found: 452.2347.

EXAMPLE 14

1-Naphthylmethyl-[3-(3-fluorophenyl)-isoxazol-5-yl]-(3-azepin-1-yl-propyl)-amine TFA salt

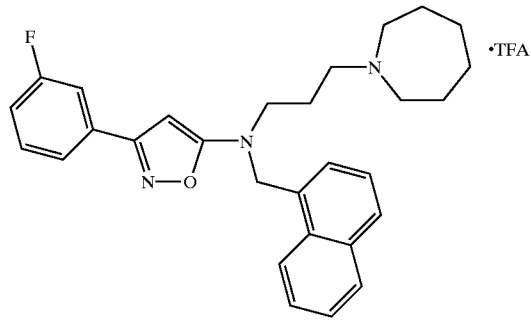

HRMS (ES): M+1 calc. for $C_{29}H_{32}FN_3O_1$: 458.2602, found: 458.2585.

EXAMPLE 15

3,4-Methylenedioxybenzyl-[3-(4-fluorophenyl)-isoxazol-5-yl]-(3-azepin-1-yl-propyl)-amine TFA salt

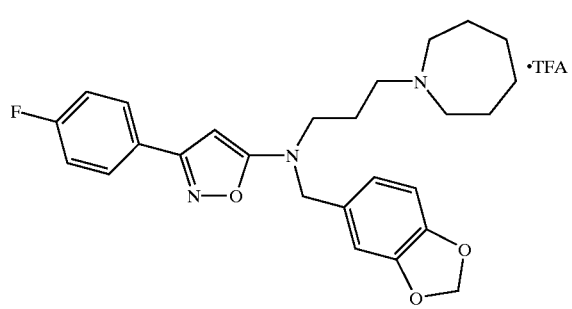

HRMS (ES): M+1 calc. for $C_{26}H_{30}FN_3O_3$: 452.2344, found: 452.2348.

EXAMPLE 16

1-Naphthylmethyl-[3-(4-fluorophenyl)-isoxazol-5-yl]-(3-azepin-1-yl-propyl)-amine TFA salt

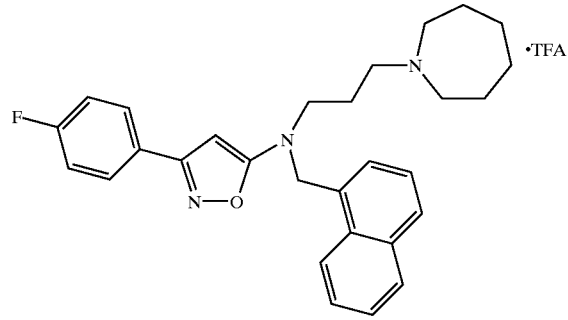

HRMS (ES): M+1 calc. for $C_{29}H_{32}FN_3O$: 458.2602, found: 458.2585.

EXAMPLE 17

3,4-Methylenedioxybenzyl-[3-(3-iodophenyl)-isoxazol-5-yl]-(3-azepin-1-yl-propyl)-amine TFA salt

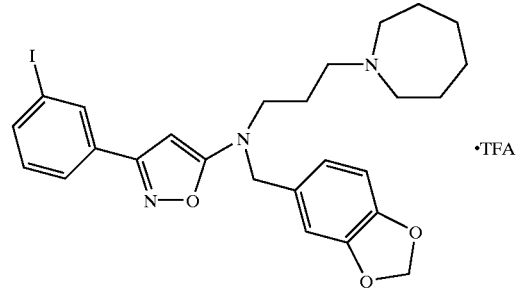

HRMS (ES): M+1 calc. for $C_{26}H_{30}IN_3O_3$: 560.1404, found: 560.1412.

EXAMPLE 18

1-Naphthylmethyl-[3-(3-iodophenyl)-isoxazol-5-yl]-(3-azepin-1-yl-propyl)-amine TFA salt

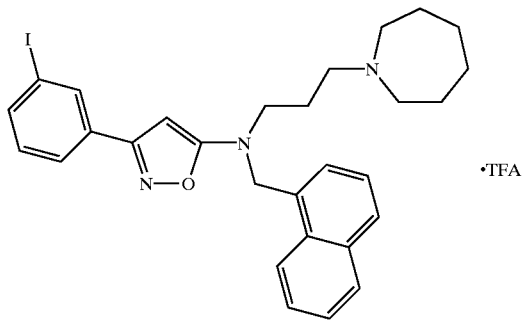

HRMS (ES): M+1 calc. for $C_{29}H_{32}IN_3O$: 566.1663, found: 566.1633.

EXAMPLE 19

3,4-Methylenedioxybenzyl-[3-(4-iodophenyl)-isoxazol-5-yl]-(3-azepin-1-yl-propyl)-amine TFA salt

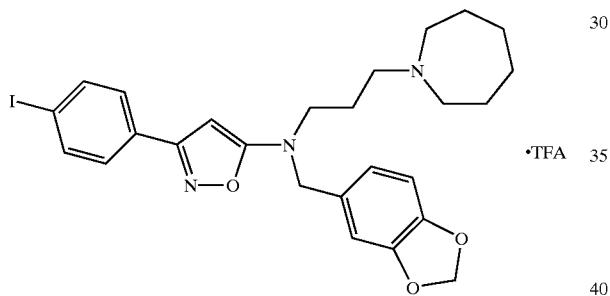

HRMS (ES): M+1 calc. for $C_{26}H_{30}IN_3O_3$: 560.1404, found: 560.1427.

EXAMPLE 20

1-Naphthylmethyl-[3-(4-iodophenyl)-isoxazol-5-yl]-(3-azepin-1-yl-propyl)-amine TFA salt

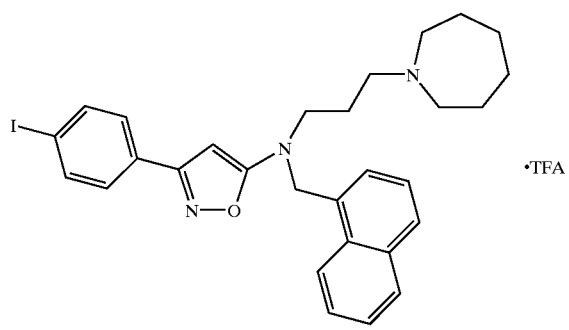

HRMS (ES): M+1 calc. for $C_{29}H_{32}IN_3O$: 566.1663, found: 566.1639.

EXAMPLE 21

3,4-Methylenedioxybenzyl-[3-(2,3-dichloro-phenyl)-isoxazol-5-yl]-(3-azepin-1-yl-propyl)-amine TFA salt

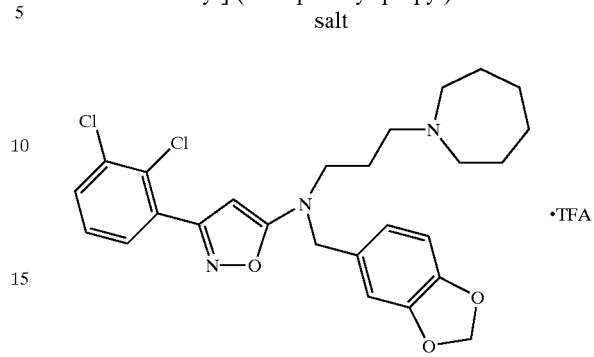

HRMS (ES): M+1 calc. for $C_{26}H_{29}Cl_2N_3O_3$: 502.1659, found: 502.1687.

EXAMPLE 22

1-Naphthylmethyl-[3-(2,3-dichlorophenyl)-isoxazol-5-yl]-(3-azepin-1-yl-propyl)-amine TFA salt

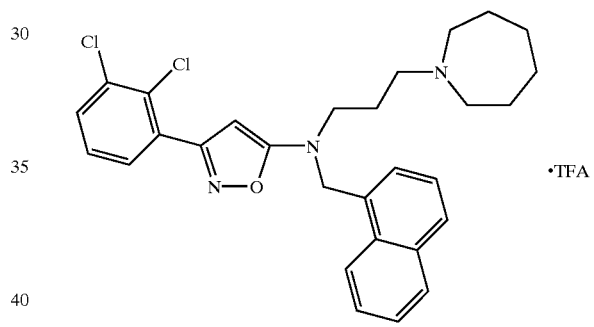

HRMS (ES): M+1 calc. for $C_{29}H_{31}Cl_2N_3O$: 508.1917, found: 508.1922.

EXAMPLE 23

3,4-Methylenedioxybenzyl-[3-(2,4-dichloro-phenyl)-isoxazol-5-yl](3-azepin-1-yl-propyl)-amine TFA salt

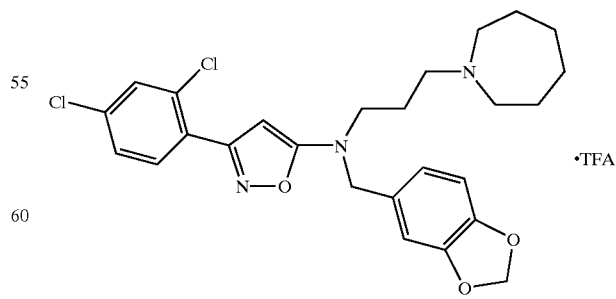

HRMS (ES): M+1 calc. for $C_{26}H_{29}Cl_2N_3O_3$: 502.1659, found: 502.1649.

EXAMPLE 24

3,4-Methylenedioxybenzyl-[3-(3,4-dichloro-phenyl)-isoxazol-5-yl]-(3-azepin-1-yl-propyl)-amine TFA salt

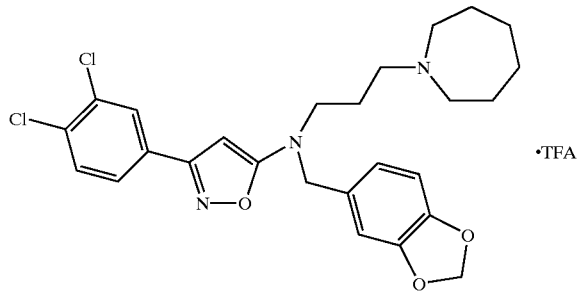

HRMS (ES): M+1 calc. for $C_{26}H_{29}Cl_2N_3O_3$: 502.1659, found: 502.1682.

EXAMPLE 25

1-Naphthylmethyl-[3-(3,4-dichlorophenyl)-isoxazol-5-yl]-(3-azepin-1-yl-propyl)-amine TFA salt

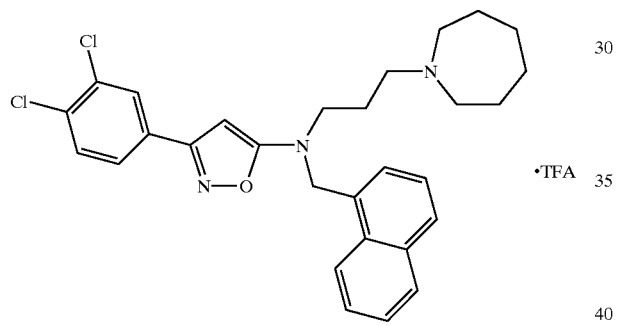

HRMS (ES): M+1 calc. for $C_{29}H_{31}Cl_2N_3O$: 508.1917, found: 508.1907.

EXAMPLE 26

3,4-Methylenedioxybenzyl-[3-(3,4-difluorophenyl)-isoxazol-5-yl]-(3-azepin-1-yl-propyl)-amine TFA salt

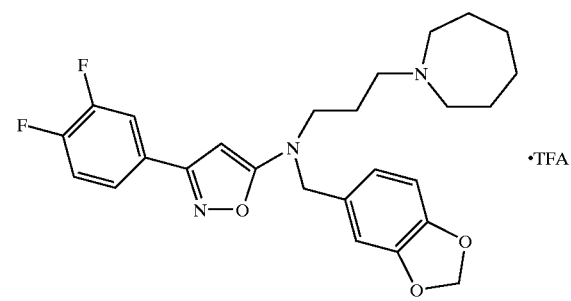

HRMS (ES): M+1 calc. for $C_{26}H_{29}F_2N_3O_3$: 470.2250, founfd: 470.2253.

EXAMPLE 27

3,4-Methylenedioxybenzyl-[3-(2-methylphenyl)-isoxazol-5-yl]-(3-azepin-1-yl-propyl)-amine TFA salt

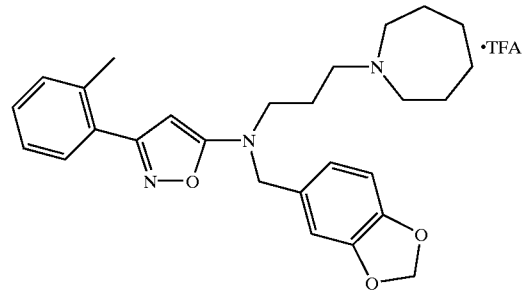

HRMS (ES): M+1 calc. for $C_{27}H_{33}N_3O_3$: 448.2594, found: 448.2590.

EXAMPLE 28

1-Naphthylmethyl-[3-(2-methylphenyl)-isoxazol-5-yl]-(3-azepin-1-yl-propyl)-amine TFA salt

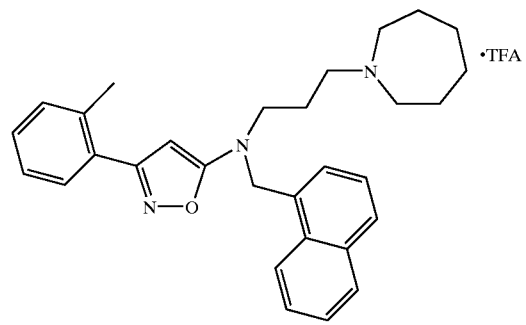

HRMS (ES): M+1 calc. for $C_{30}H_{35}N_3O$: 454.2853, found: 454.2852.

EXAMPLE 29

3,4-Methylenedioxybenzyl-[3-(3-methylphenyl)-isoxazol-5-yl]-(3-azepin-1-yl-propyl)-amine TFA salt

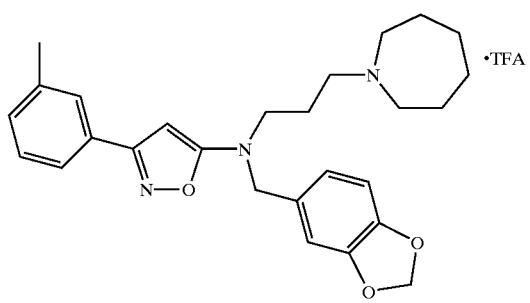

HRMS (ES): M+1 calc. for $C_{27}H_{33}N_3O_3$: 448.2594, found: 448.2594.

EXAMPLE 30

3,4-Methylenedioxybenzyl-[3-(4-methylphenyl)-isoxazol-5-yl]-(3-azepin-1-yl-propyl)-amine TFA salt

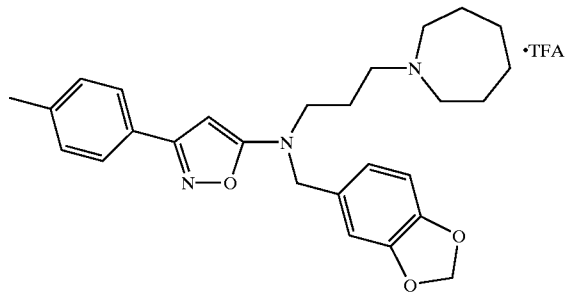

HRMS (ES): M+1 calc. for $C_{27}H_{33}N_3O_3$: 448.2594, found: 448.2590.

EXAMPLE 31

1-Naphhylmethyl-[3-(4-methylphenyl)-isoxazol-5-yl]-(3-azepin-1-yl-propyl)-amine TFA salt

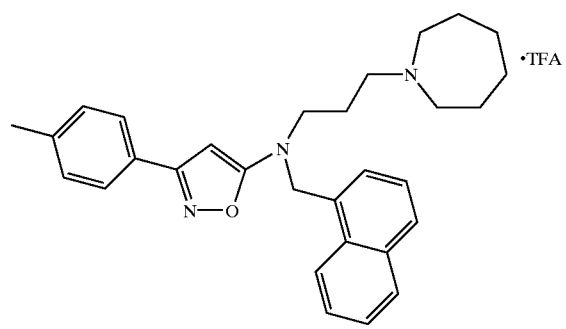

HRMS (ES): M+1 calc. for $C_{30}H_{35}N_3O$: 454.2853, found: 454.2854.

EXAMPLE 32

3,4-Methylenedioxybenzyl-[3-(3-trifluoromethyl-phenyl)-isoxazol-5-yl]-(3-azepin-1-yl-propyl)-amine TFA salt

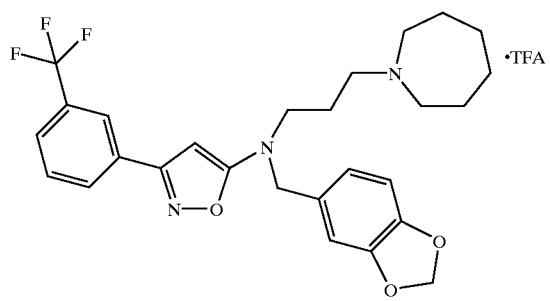

HRMS (ES): M+1 calc. for $C_{27}H_{30}F_3N_3O_3$: 502.2312, found: 502.2322.

EXAMPLE 33

1-Naphthylmethyl-[3-(3-trifluoromethylphenyl)-isoxazol-5-yl]-(3-azepin-1-yl-propyl)-amine TFA salt

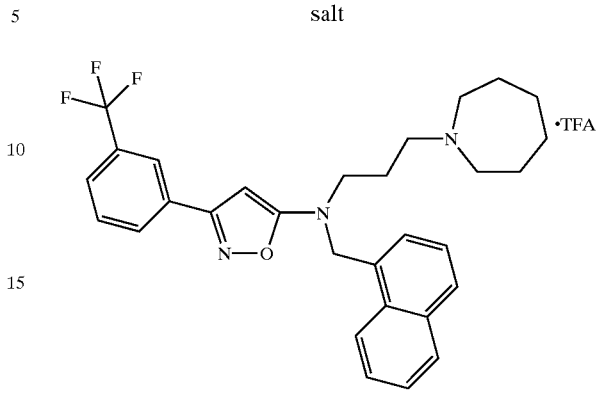

HRMS (ES): M+1 calc. for $C_{30}H_{32}F_3N_3O$: 508.257, found: 508.2545.

EXAMPLE 34

3,4-Methylenedioxybenzyl[3-(4-trifluoromethylphenyl)-isoxazol-5-yl]-(3-azepin-1-yl-propyl)-amine TFA salt

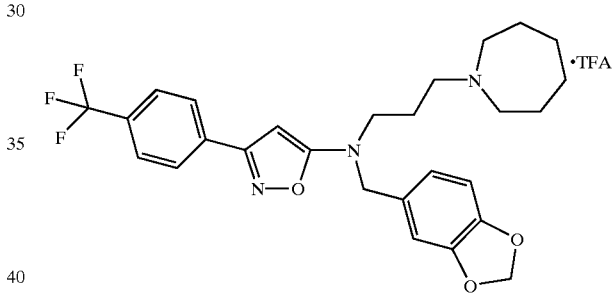

HRMS (ES): M+1 calc. for $C_{27}H_{30}F_3N_3O_3$: 502.2312, found: 502.2323.

EXAMPLE 35

1-Naphthylmethyl-[3-(4-trifluoromethylphenyl)-isoxazol-5-yl]-(3-azepin-1-yl-propyl)-amine TFA salt

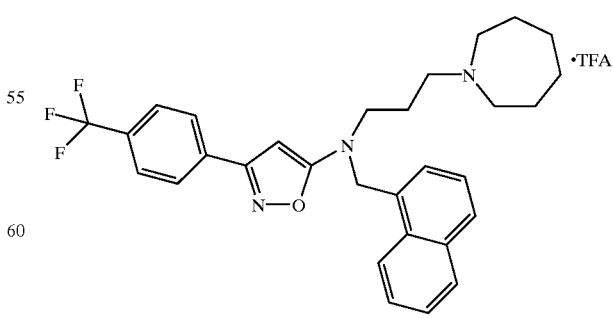

HRMS (ES): M+1 calc. for $C_{30}H_{32}F_3N_3O$: 508.2576, found: 508.2536.

EXAMPLE 36

3,4-Methylenedioxybenzyl-[3-(2-methoxyphenyl)-isoxazol-5-yl]-(3-azepin-1-yl-propyl)-amine TFA salt

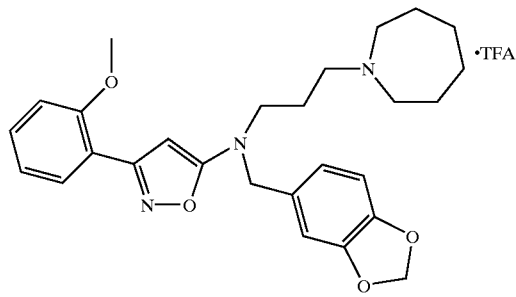

HRMS (ES): M+1 calc. for $C_{27}H_{33}N_3O_4$: 464.2544, found: 464.2532.

EXAMPLE 37

3,4-Methylenedioxybenzyl-[3-(3-methoxyphenyl)-isoxazol-5-yl]-(3-azepin-1-yl-propyl)-amine TFA salt

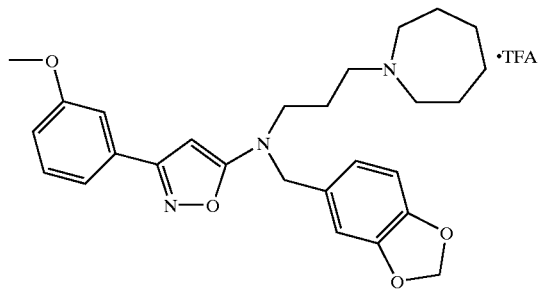

HRMS (ES): M+1 calc. for $C_{27}H_{33}N_3O_4$: 464.2544, found: 464.2535.

EXAMPLE 38

1-Naphthylmethyl-[3-(3-methoxyphenyl)-isoxazol-5-yl]-(3-azepin-1-yl-propyl)-amine TFA salt

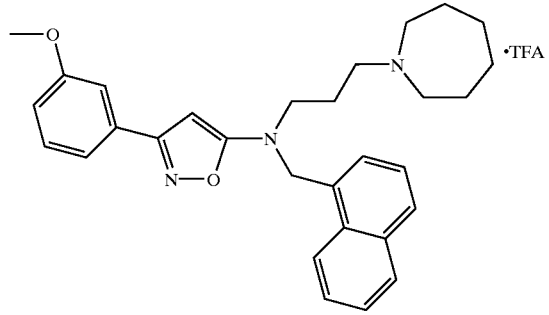

HRMS (ES): M+1 calc. for $C_{30}H_{35}N_3O_2$: 470.2802, found: 470.2813.

EXAMPLE 39

3,4-Methylenedioxybenzyl-[3-(4-methoxyphenyl)-isoxazol-5-yl]-(3-azepin-1-yl-propyl)-amine TFA salt

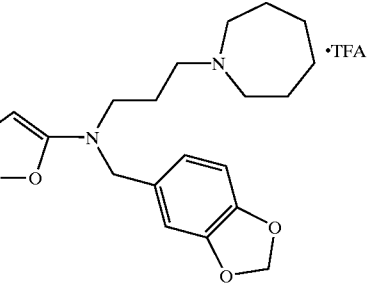

HRMS (ES): M+1 calc. for $C_{27}H_{33}N_3O_4$: 464.2544, found: 464.2530.

EXAMPLE 40

1-Naphthylmethyl-[3-(4-methoxyphenyl)-isoxazol-5-yl]-(3-azepin-1-yl-propyl)-amine TFA salt

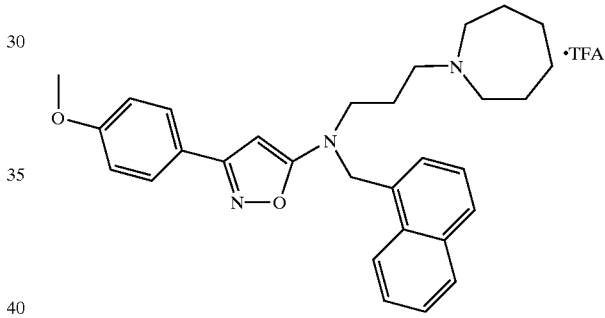

HRMS (ES): M+1 calc. for $C_{30}H_{35}N_3O_2$: 470.2802, found: 470.2822.

EXAMPLE 41

3,4-Methylenedioxybenzyl-[3-(3,4-dimethoxyphenyl)-isoxazol-5-yl]-(3-azepin-1-yl-propyl)-amine TFA salt HRMS (ES): M+1 calc. for $C_{28}H_{35}N_3O_5$: 494.2649, found: 494.2641.

EXAMPLE 42

3,4-Methylenedioxybenzyl-[3-(3,5-dimethoxyphenyl)-isoxazol-5-yl]-(3-azepin-1-yl-propyl)-amine TFA salt

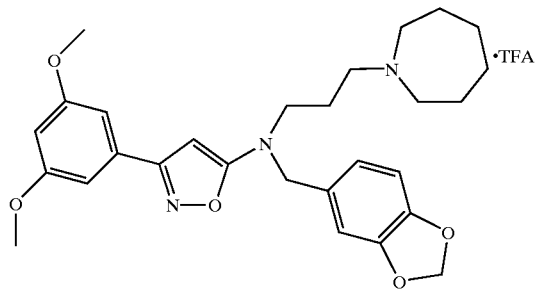

HRMS (ES): M+1 calc. for $C_{28}H_{35}N_3O_5$: 494.2649, found: 494.2646.

EXAMPLE 43

3,4-Methylenedioxybenzyl-[3-(3,4-methylenedioxyphenyl)-isoxazol-5-yl]-(3-azepin-1-yl-propyl)-amine TFA salt

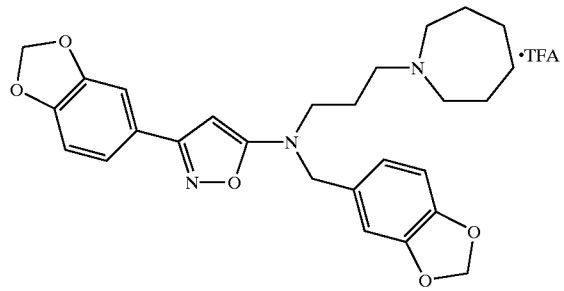

HRMS (ES): M+1 calc. for $C_{27}H_{31}N_3O_5$: 478.2336, found: 478.2339.

EXAMPLE 44

3,4-Methylenedioxybenzyl-[3-(3-fluoro-4-methylphenyl)-isoxazol-5-yl]-(3-azepin-1-yl-propyl)-amine TFA salt

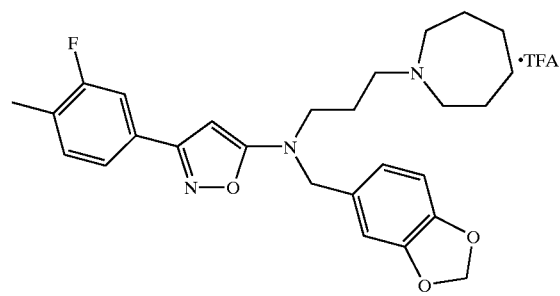

HRMS (ES): M+1 calc. for $C_{27}H_{32}FN_3O_3$: 466.25, found 466.2491.

EXAMPLE 45

3,4-Methylenedioxybenzyl-[3-(3-fluoro-4-methoxyphenyl)-isoxazol-5-yl]-(3-azepin-1-yl-propyl)-amine TFA salt

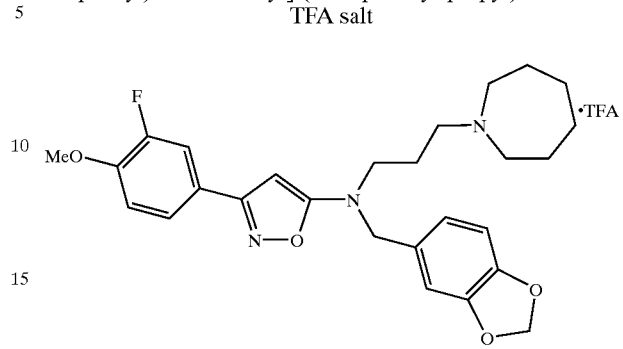

HRMS (ES): M+1 calc. for $C_{27}H_{32}FN_3O_4$: 482.2449, found: 482.2441.

EXAMPLE 46

3,4-Methylenedioxybenzyl-[3-(4-thiomethylphenyl)-isoxazol-5-yl]-(3-azepin-1-yl-propyl)-amine TFA salt

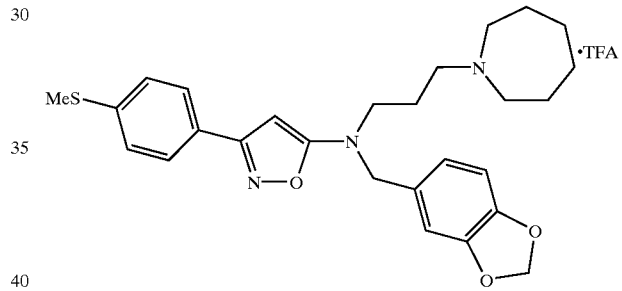

MS (ES): M+1=480.2

EXAMPLE 47

1-Naphthylmethyl-[3-(4-thiomethylphenyl)-isoxazol-5-yl]-(3-azepin-1-yl-propyl)-amine TFA salt

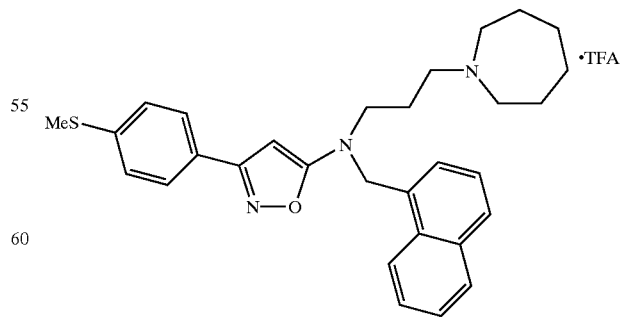

HRMS (ES): M+1 calc. for $C_{30}H_{35}N_3O_3S$: 486.2573, found: 486.2574.

EXAMPLE 48

3,4-Methylenedioxybenzyl-[3-(4-methylsulfoxide-phenyl)-isoxazol-5-yl]-(3-azepin-1-yl-propyl)-amine TFA salt

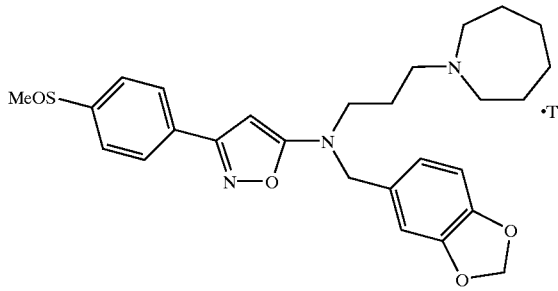

Step A: 3-(4-methylsulfoxide-phenyl)-5-chloro-isoxazole

To a solution of 3-(4-thiomethylphenyl)-5-chloroisoxazole (581 mg, 2.57 mmol), in methanol (40 ml) cooled to 0° C. is added sodium periodate (578 mg, 2.7 mmol) in water (5 ml) slowly. The reaction mixture is stirred at room temperature for 18 hrs, filtered on cellite and concentrated in vacuo. The crude residue is taken in ethyl acetate, washed with water and brine, dried over sodium sulfate, and concentrated in vacuo. The crude material is purified by flash chromatography (silica gel, dichloromethane to 5% methanol in dichloromethane) to give 3-(4-methylsulfoxide-phenyl)-5-chloro-isoxazole.

$^1$H NMR (CDCl$_3$, 400 Mhz): δ7.92 (d, 2H, 10 Hz); 7.76 (d, 2H, 10 Hz); 6.54 (s, 1H); 2.75 (s, 3H).

Step B: 3-(4-methylsulfoxide-phenyl)-isoxazol-5-yl-(3-azepin-1-yl-propyl)-amine A mixture of 3-(4-methylsulfoxide-phenyl)-5-chloro-isoxazole (50 mg, 0.21 mmol) and 3-azepin-propylamine in DMSO (0.5 ml) was heated at 50° C. for 18 hrs. The reaction mixture is partitioned between dilute sodium bicarbonate and ethyl acetate. The organic layer is dried over sodium sulfate, and concentrated in vacuo. The crude material is purified by flash chromatography (silica gel,, 6% to 10% methanol containing 10% NH$_4$OH in dichloromethane) to give [3-(4-methylsulfoxide-phenyl)-isoxazol-5-yl]-(3-azepin-1-yl-propyl)-amine.

$^1$H NMR (CDCl$_3$, 400 Mhz): δ7.92 (d, 2H, 10 Hz); 7.68 (d, 2H, 10 Hz); 7.40 (broad t, 1H); 5.23 (s, 1H);3.40–3.30 (m, 2H); 2.76 (s, 3H); 2.70–2.60 (m, 6H); 1.84–1.60 (m, 10H).

Step C: 3,4-Methylenedioxybenzyl-[3-(4-methylsulfoxide-phenyl)-isoxazol-5-yl]-(3-azepin-1-yl-propyl)-amine TFA salt To a solution of [3-(4-methylsulfoxide-phenyl)-isoxazol-5-yl]-(3-azepin-1-yl-propyl)-amine (31 mg, 0.086 mmol) in DMF (2 ml) is added NaH (8.6 mg, 60% in oil, 0.21 mmol). After 5 min is added 3,4-Methylenedioxybenzyl chloride (0.033 ml, 50% by weight in dichloromethane, 0.13 mmol). After 15 min, the reaction mixture is diluted with water, extracted with ethyl acetate and the organic layer is washed with aqueous LiCl, dried over sodium sulfate, and concentrated in vacuo. The residue is purified by preparative HPLC (20×50 mm C18, 0.1%TFA ACN/water gradient) to provide after solvent evaporation: 3,4-methylenedioxybenzyl-[3-(4-methylsulfoxide-phenyl)-isoxazol-5-yl]-(3-azepin-1-yl-propyl)-amine TFA salt.

HRMS (ES): M+1 calc. for C$_{27}$H$_{33}$N$_3$O$_4$S: 496.2264, found: 496.2273.

EXAMPLE 49

3,4-Methylenedioxybenzyl-[3-(4-methylsulfone-phenyl)-isoxazol-5-yl]-(3-azepin-1-yl-propyl)-amine TFA salt

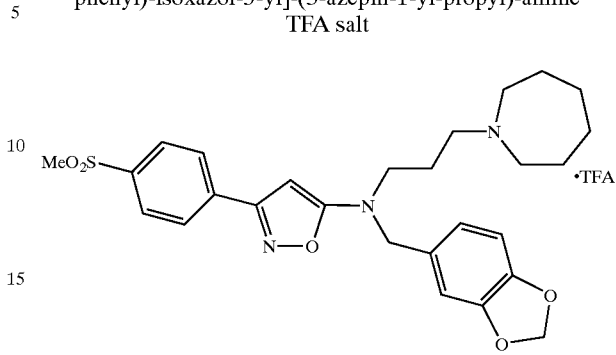

Step A: 3-(4-methylsulfone-phenyl)-5-chloro-isoxazole

To a solution of 3-(4-thiomethylphenyl)-5-chloro-isoxazole (430 mg, 1.91 mmol), in dichloromethane (20 ml) cooled to 0° C. is slowly added m-CPBA (739 mg, 2.48 mmol). After 20 min, the reaction mixture is partitioned between diethyl ether and dilute sodium bicarbonate. The organic layer is washed with brine, dried over sodium sulfate, and concentrated in vacuo. The crude material is purified by flash chromatography (silica gel, 35% to 50% ethyl acetate in hexane) to provide give 3-(4-methylsulfone-phenyl)-5-chloro-isoxazole.

$^1$H NMR (CDCl$_3$, 400 Mhz): δ8.07 (d, 2H, 10 Hz); 7.97 (d, 2H, 10 Hz); 6.56 (s, 1H); 3.10 (s, 3H).

Step B: 3,4-Methylenedioxybenzyl-[3-(4-methylsulfone-phenyl)-isoxazol-5-yl]-(3-azepin-1-yl-propyl)-amine TFA salt is prepared following a similar protocol as described in example 48

HRMS (ES): M+1 calc. for C$_{27}$H$_{33}$N$_3$O$_5$S: 512.2213, found: 512.2206.

EXAMPLE 50

3,4-Methylenedioxybenzyl-[3-(3-cyanophenyl)-isoxazol-5-yl]-(3-azepin-1-yl-propyl)-amine TFA salt

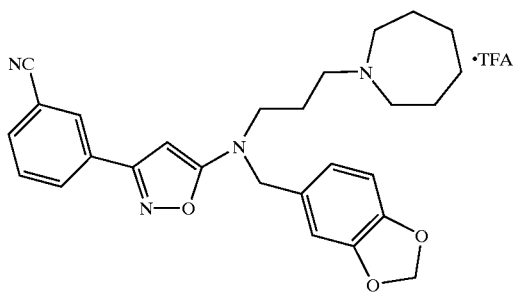

HRMS (ES): M+1 calc. for C$_{27}$H$_{30}$N$_4$O$_3$: 459.239, found: 459.2374.

EXAMPLE 51

1-Naphthylmethyl-[3-(3-cyanophenyl)-isoxazol-5-yl]-(3-azepin-1-yl-propyl)-amine TFA salt

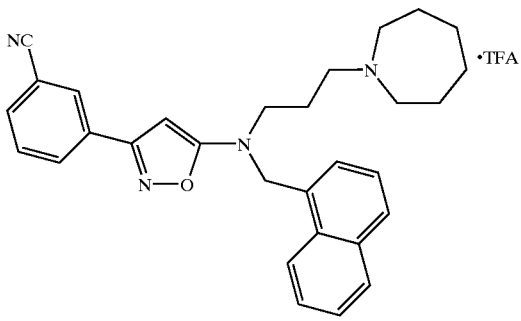

3-(3-cyanophenyl)-5-chloro-isoxazole is prepared using a similar protocol as described in example 3. The title compound is then derived from 3-(3-cyanophenyl)-5-chloroisoxazole using a similar protocol as described in example 48 (1-Naphthylmethyl bromide is used instead of 3,4-methylenedioxybenzyl chloride).

HRMS (ES): M+1 calc. for $C_{30}H_{32}N_4O$: 465.2649, found: 465.2657.

EXAMPLE 52

3,4-Methylenedioxybenzyl-[3-(3-nitrophenyl)-isoxazol-5-yl]-(3-azepin-1-yl-propyl)-amine TFA salt

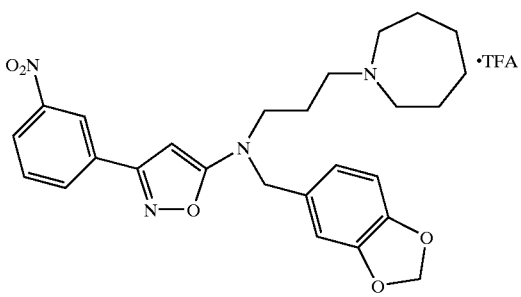

Prepared following a similar protocol as described in example 48:

HRMS (ES): M+1 calc. for $C_{26}H_{30}N_4O_5$: 479.2289, found: 479.2274.

EXAMPLE 53

1-Naphthylmethyl-[3-(3-nitrophenyl)-isoxazol-5-yl]-(3-azepin-1-yl-propyl)-amine TFA salt

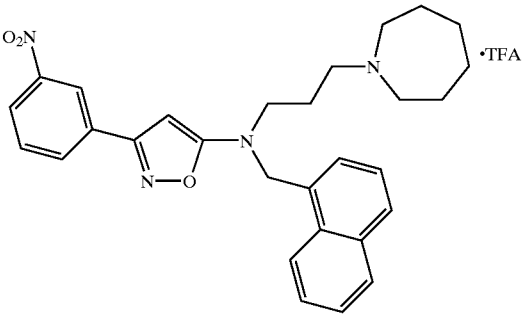

Prepared following a similar protocol as described in example 48:

HRMS (ES): M+1 calc. for $C_{29}H_{32}N_4O_3$: 485.2547, found: 485.2540.

EXAMPLE 54

3,4-Methylenedioxybenzyl-[3-(3-biphenyl)-isoxazol-5-yl]-(3-azepin-1-yl-propyl)-amine TFA salt

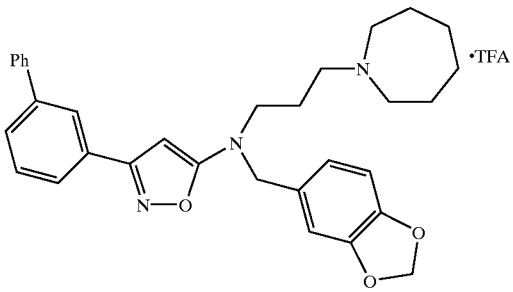

To a solution of 3-(3-iodophenyl)-5-chloro-isoxazole (100 mg, 0.33 mmol, example 8a) in toluene (5 ml) is added phenyl boronic acid (52 mg, 0.43 mmol), powdered potassium carbonate (136 mg, 0.98 mmol), and Pd(PPh$_3$)$_4$ (38 mg, 0.03 mmol) and the reaction mixture is stirred at 100° C. for 18 hrs. The reaction mixture is diluted with diethyl ether and filtered on a small plug of silica gel. The crude material is purified by flash chromatography (silica gel, 25 to 4% diethyl ether in hexane) to provide 3-(3-biphenyl)-5-chloro-isoxazole.

$^1$H NMR (CDCl$_3$, 400 Mhz): δ8.10–7.88 (m, 1H); 7.76–7.66 (m, 2H); 7.64–7.60 (m, 2H); 7.58–7.50 (m, 1H); 7.50–7.44 (m, 2H); 7.42–7.36 (m, 1H); 6.54 (s, 1H).

The title compound is then derived from 3-(3-biphenyl)-5-chloro-isoxazole following a similar protocol as described in example 3.

HRMS (ES): M+1 calc. for $C_{32}H_{35}N_3O_3$: 510.2751, found: 510.2752.

EXAMPLE 55

3,4-Methylenedioxybenzyl-[3-(4-biphenyl)-isoxazol-5-yl]-(3-azepin-1-yl-propyl)-amine TFA salt

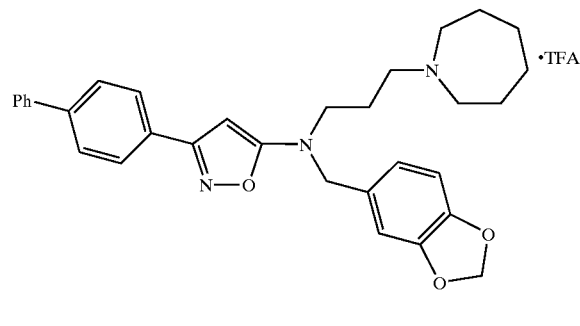

Prepared following a similar protocol as described in example 54 while starting from 3-(4-iodophenyl)-5-chloro-isoxazole):

HRMS (ES): M+1 calc. for $C_{32}H_{35}N_3O_3$: 510.2751, found: 510.2749.

EXAMPLE 56

3,4-Methylenedioxybenzyl-[3-(2-naphthyl)-isoxazol-5-yl]-(3-azepin-1-yl-propyl)-amine TFA salt

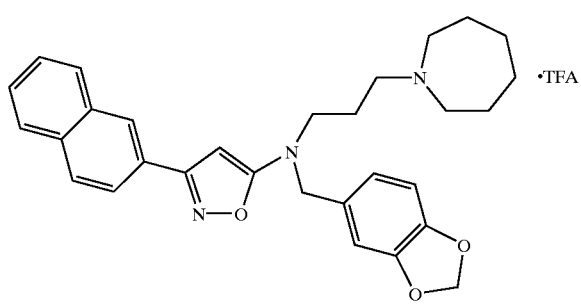

Prepared following a similar protocol as described in example 3:

HRMS (ES): M+1 calc. for $C_{30}H_{33}N_3O_3$: 484.2595, found: 484.2609.

EXAMPLE 57

1-Naphthylmethyl-[3-(2-naphthyl)-isoxazol-5-yl]-(3-azepin-1-yl-propyl)-amine TFA salt

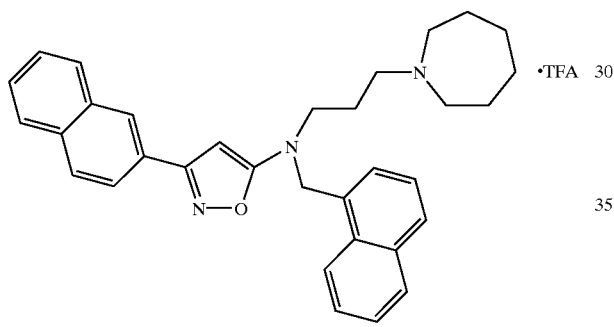

Prepared following a similar protocol as described in example 3:

HRMS (ES): M+1 calc. for $C_{33}H_{35}N_3O$: 490.2853, found: 490.2841.

EXAMPLE 58

3,4-Methylenedioxybenzyl-[3-(2-furyl)-isoxazol-5-yl]-(3-azepin-1-yl-propyl)-amine TFA salt

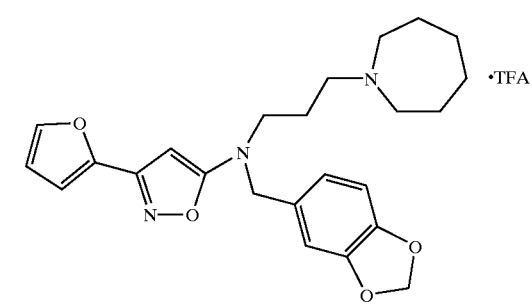

Prepared following a similar protocol as described in example 3:

HRMS (ES): M+1 calc. for $C_{24}H_{29}N_3O_4$: 424.2231, found: 424.2235.

EXAMPLE 59

1-Naphthylmethyl-[3-(2-furyl)-isoxazol-5-yl]-(3-azepin-1-yl-propyl)-amine TFA salt

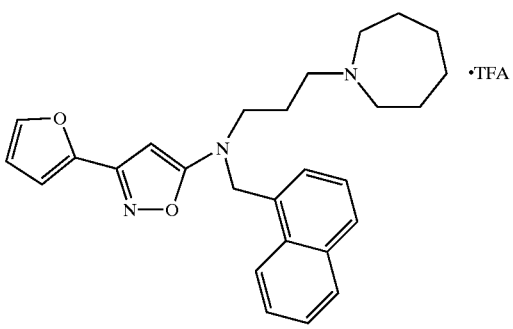

Prepared following a similar protocol as described in example 3:

HRMS (ES): M+1 calc. for $C_{27}H_{31}N_3O_2$: 430.2489, found: 430.2489.

EXAMPLE 60

3,4-Methylenedioxybenzyl-[3-(3-furyl)isoxazol-5-yl]-(3-azepin-1-yl-propyl)amine TFA salt

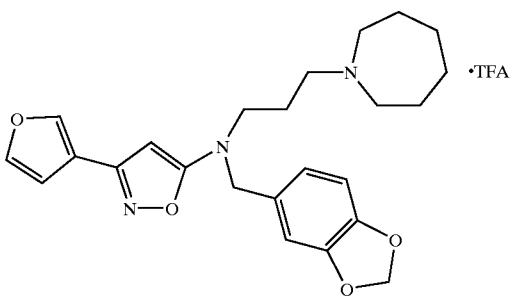

Prepared following a similar protocol as described in example 3:

HRMS (ES): M+1 calc. for $C_{24}H_{29}N_3O_4$: 424.2231, found: 424.2235.

EXAMPLE 61

1-Naphthylmethyl-[3-(3-furyl)isoxazol-5-yl]-(3-azepin-1-yl-propyl)amine TFA salt

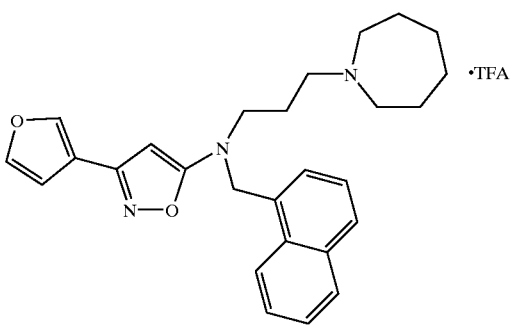

Prepared following a similar protocol as described in example 3:

HRMS (ES): M+1 calc. for $C_{27}H_{31}N_3O_2$: 430.2489, found: 430.2482.

EXAMPLE 62

Naphthalen-1-ylmethyl-(3-phenyl-isoxazol-5-yl)-(3-piperidin-yl-propyl)-amine ©: where R=piperidine and R'=1-methylnaphthalene

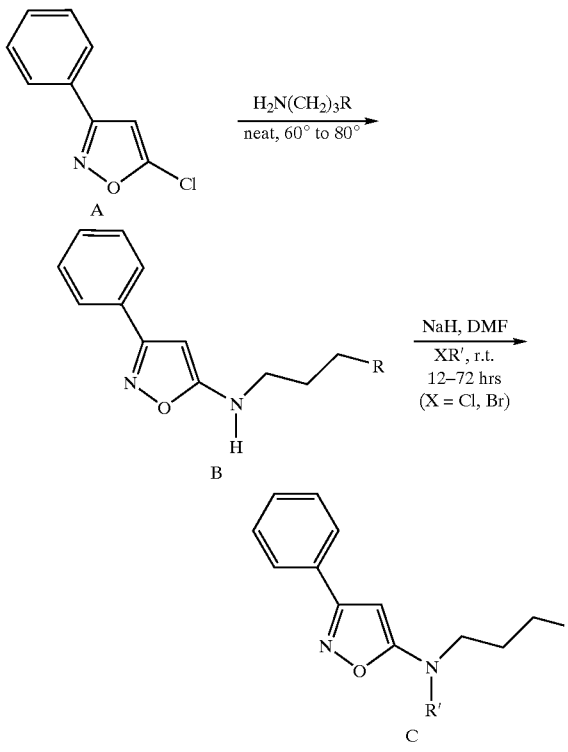

Step 1: 3-Phenyl-isoxazol-5-yl-(3-piperidin-1-yl-propyl)-amine(B); where R=piperidine METHOD 1: To 1-(3-aminopropyl)piperidine ( 0.227 gm 0.0016 m) was added tetrahydrofuran(4 ml). The solution was cooled to −78 and 1 ml 1.6 M n-Butyl lithium was added over 15 minutes. Allow the solution to warm up to −30 for 15 minutes. After cooling back down to −78, a solution of 0.286 gm (0.0016m) 5-phenyl-3-chloroisoxazole was added over 10 minutes. Let stir at room temperature over night. Ethyl acetate (15 ml) was added and the solution was washed with sodium bicarbonate (saturated, aqueous) and brine. Dry over sodiumsulfate, filter, and concentrate to an oil. Purification by flash chromatography (30 mm-5 inches silica, methylene chloride 97, methanol 3, ammonium hydroxide 0.3) gave 0.093 gm. (20%)

HPLC: 96.05%; Mass Spectra Cal'd.=285.39; Found: 286.1.

Analysis:

Cal.'d for $C_{17}H_{23}N_3O.0.15\ CH_2Cl_2+0.5\ H_2O$ C, 67.06; H, 7.97; N, 13.68.

Found: C, 66.99; H, 7.78; N, 14.06.

METHOD 2: To 3.53 gms (0.0248 m) 1-(3-aminopropyl)piperidine was added 2.2 gms (0.0124 m) 5-phenyl-3-chloroisoxazole. The reaction was heated at 60° for 48 hours. The cooled mixture was dissolved in ethyl acetate and washed with sodium carbonate-sodium bicarbonate (aqueous, saturated), dried over sodium sulfate, filtered and concentrated to an oil. Purification by flash chromatograph (50 mm×5 inches silica, methylene chloride (95), methanol (5) ammonium hydroxide (0.5)) gave 2.0 gms of "title". Identical to a sample produced in method 1.

Step 2: Naphthalene-1-ylmethyl-(3-phenyl-isoxazol-5-yl)-(3-piperidin-yl-propyl)-amine To a solution of 3-phenyl-isoxazol-5-yl-(3-piperidin-1-yl-propyl)amine (142.5 mg, 0.0005 m) in DMF (6 ml) was added 25 mg 60% sodium hydride in oil. The reaction foamed and turned yellow. After stirring for 5 minutes, 110.5 mg 1-(bromomethyl)naphthalene in DMF (3 ml) was added. The reaction turned from yellow to brown in color. The DMF was removed under reduced pressure. The oil was flash chromatographed using a 50 mm×6" silica gel column with methylene chloride 95-methanol 5-ammonium hydroxide 0.5 as the solvent system. The product fractions were collected and concentrated to an oil. Add hexane/ether and remove under reduced pressure (2×s). Ethanol was added followed by 1M HCl in ether (1 ml). Remove the solvent. Add hexane/ether (2×s) to yield "title" as a foam. Dry under high vac. HPLC 95.43% at 215. Mass Spectra cal'd. 425.57; found 426.4. H NMR (CDCl3) 11.95–11.75(br,s,1H), 8.1–7.3(m, 12H), 5.6–5.4(s,1H), 5.2–4.8(s,2H), 3.6–3.4(br, 2H)3.35–3.15(br,2H), 2.7–2.5(br, 2H),2.3–2.0(br,6H.)

Analysis:

Cal'd. for $C_{29}H_{31}N_3O.HCl.0.25\ C_4H_{10}O+0.85H_2O$ C, 70.24; H, 7.36; N, 8.47.

Found: C, 70.06; H, 6.96; N, 8.09.

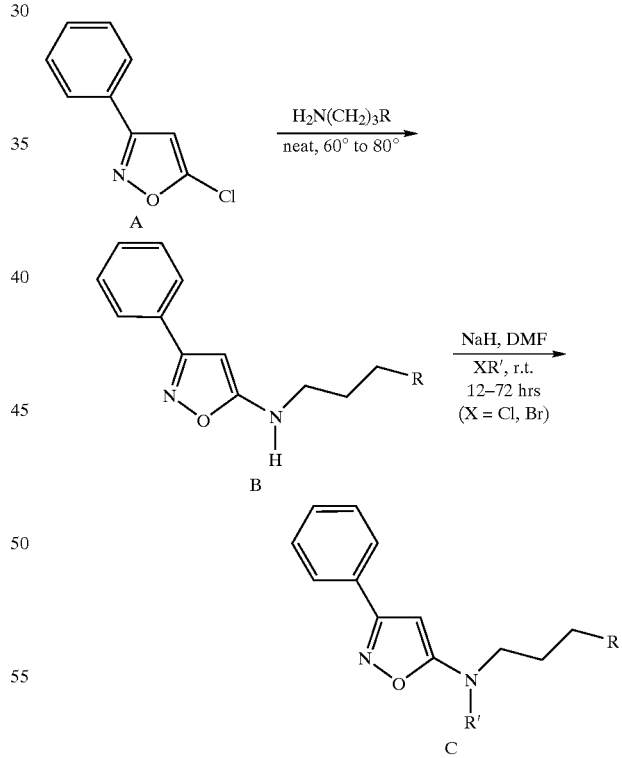

EXAMPLE 63

Table 1 contains compounds C obtained from the above sequence described in EXAMPLE 62. These compounds were individually prepared and characterized by NMR, Mass Spectra, HPLC and C,H,N analysis.

TABLE 1

| R | R' | Analysis |
|---|---|---|
| cyclohexyl | benzyl | HPLC 97.27% at 215 nm<br>Mass Spec = 376.3 |
| pyrrolidinyl | benzyl | HPLC 92.78% at 215 nm<br>Mass Spec = 362.2 |
| imidazolyl | benzyl | HPLC 90.53% at 215 nm<br>Mass Spec = 359 |
| N,N-diethylamino | benzyl | HPLC 98.43% at 215 nm<br>Mass Spec = 364 |
| morpholinyl | benzyl | HPLC 95.91% at 215 nm<br>Mass Spec = 378 |
| 2-methylpiperidinyl | naphthylmethyl | HPLC 90.15% at 215 nm<br>Mass Spec = 440.3 |
| 2-methylpiperidinyl | 3,5-dimethoxybenzyl | HPLC 85.44% at 215 nm<br>Mass Spec = 450.4 |
| 4-methylpiperazinyl | naphthylmethyl | HPLC 91.82% at 215 nm<br>Mass Spec = 441.3 |
| 4-methylpiperazinyl | 3,5-dimethoxybenzyl | HPLC 94.32% at 215 nm<br>Mass Spec = 451.3 |

EXAMPLE 64

Substituted-(3-Phenyl-isoxazol-5-yl)-(piperin-1-ylpropyl)-amines

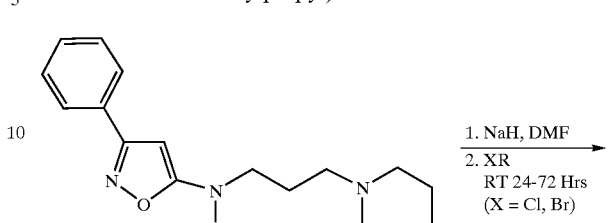

1. NaH, DMF
2. XR
RT 24–72 Hrs
(X = Cl, Br)

Table 2 contains 17 examples of products obtained from the reaction of B to C by procedures similar to that described in EXAMPLE 62 These compounds were isolated by column chromatograph and were characterized by HPLC, Mass Spectra, C,H,N Analysis, and NMR (consistent with structures).

TABLE 2

| R | Analysis |
|---|---|
| benzyl | HPLC 97.27% AT 215<br>MS = 376.3 |
| 2-chlorobenzyl | HPLC 92.63% AT 215<br>MS = 410.2 |
| 3-chlorobenzyl | HPLC 95.91% AT 215<br>MS = 410.2 |
| 4-chlorobenzyl | HPLC 93.525 AT 215<br>MS = 410.2 |
| 3-cyanobenzyl | HPLC 91.21% AT 215<br>MS = 401 |
| 4-cyanobenzyl | HPLC 92.31% AT 215<br>MS = 401.1 |

TABLE 2-continued

| Structure | Data |
|---|---|
| 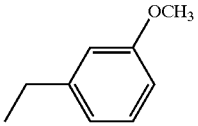 | HPLC 94.4% AT 215<br>MS = 406.1 |
| 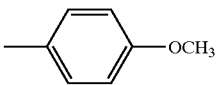 | HPLC 94.14% AT 215<br>MS = 406.1 |
| 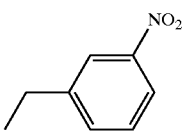 | HPLC 93.57% AT 215<br>MS = 421.3 |
| 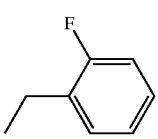 | HPLC 93.6% AT 215<br>MS = 394 |
| 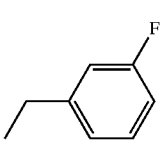 | HPLC 91.48% AT 215<br>MS = 394.2 |
| 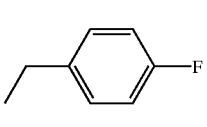 | HPLC 92.86% AT 215<br>MS = 394.2 |
| 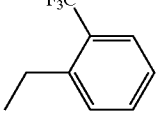 | HPLC 91.95% AT 215<br>MS = 444.2 |

TABLE 2-continued

| Structure | Data |
|---|---|
| 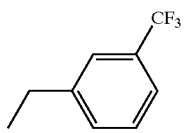 | HPLC 88.7% AT 215<br>MS = 444.3 |
|  | HPLC 95.35% AT 215<br>MS = 444 |
| 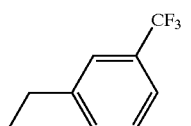 | HPLC 95.07% AT 215<br>MS = 512.3 |
| 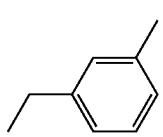 | HPLC 92.71% AT 215<br>MS = 390.3 |
| 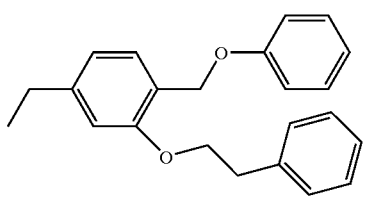 | HPLC 94.23% AT 215<br>MS = 588.4 |

EXAMPLE 65

Table 3 contains compounds made by reaction of B to C by procedures similar to those described in EXAMPLE 62. These compounds were purified by reverse phase chromatography:

TABLE 3

| Structure | Data |
|---|---|
| 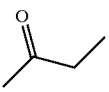 | HPLC 93.8% AT 215 MS = 342.3 |
| 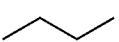 | HPLC 90.68% AT 215 MS = 328.4 |
| 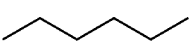 | HPLC 91.66% AT 215 MS = 342.5 |
| 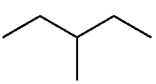 | HPLC 94.67% AT 215 MS = 355.52 |
| 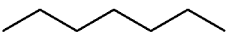 | HPLC 98.33% AT 215 MS = 370.4 |
| 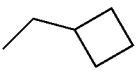 | HPLC 88.1% AT 215 MS = 354.4 |
| 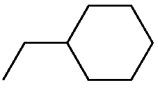 | HPLC 97.07% AT 215 MS = 382.3 |

TABLE 3-continued
| Structure | Data |
|---|---|
| 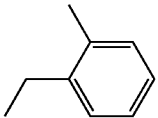 | HPLC 98.06% AT 215 MS = 390.5 |
| 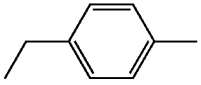 | HPLC 98.4% AT 215 MS = 390.4 |
| 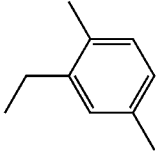 | HPLC 94.45% AT 215 MS = 404.3 |
|  | HPLC 90.72% AT 215 MS = 432.4   HPLC QUAT. 96.8% AT 215 MS = 578.4 |
| 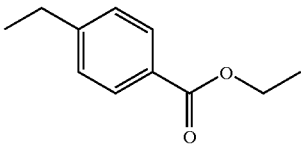 | HPLC 85.21% AT 215 MS = 434.4 |
| 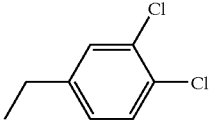 | HPLC 83.6% AT 215 MS = 444 |
| 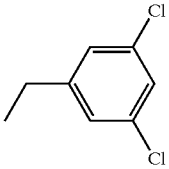 | HPLC 88.11% AT 215 MS = 446 |
| 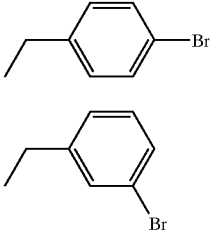 | HPLC 94.24% AT 215 MS = 456.5 |
| 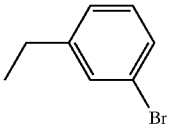 | HPLC 97.72% AT 215 MS = 456.5 |
| 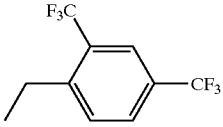 | HPLC 93.23% AT 215 MS = 512.3 |
| 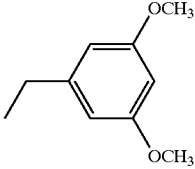 | HPLC 99.94% AT 215 MS = 436.3 |

TABLE 3-continued
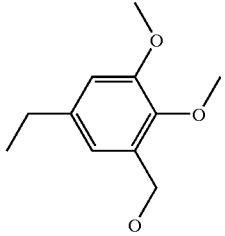 HPLC 96.02% AT 215 MS = 466.3
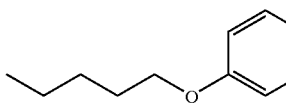 HPLC 98.83% AT 215 MS = 434.4
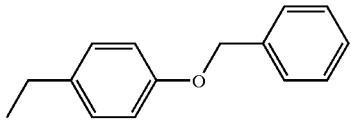 HPLC 89.97% AT 215 MS = 482
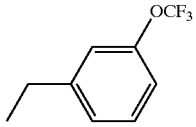 HPLC 91.99% AT 215 MS = 420.2
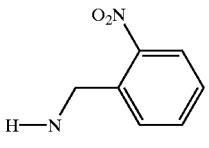 HPLC 90.50 AT 215 MS = 460.3    HPLC QUAT. 96.6% AT 215 MS = 634.3
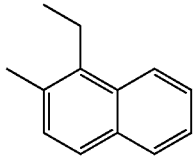 HPLC 90.28% AT 215 MS = 421.3
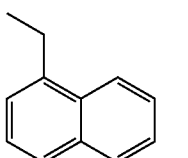 HPLC 95.99% AT 215 MS = 440.4
 HPLC 97.1% AT 215 MS = 440.3
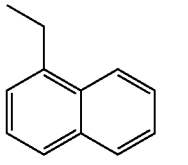 HPLC 98.84% AT 215 MS = 426.4
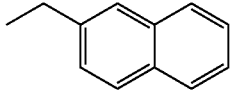 HPLC 98.84% AT 215 MS = 426.4

TABLE 3-continued

| Structure | Data |
|---|---|
| 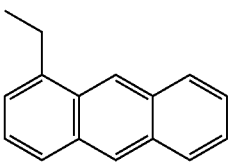 | HPLC 91.03% AT 215 MS = 476.5 |
| 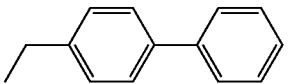 | HPLC 98.37% AT 215 MS = 452.2 |
| 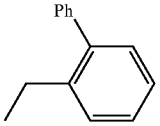 | HPLC Quat. 87.06% AT 215 MS = 618.3 |
| 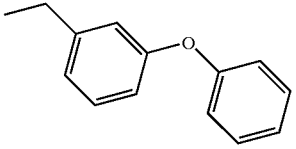 | HPLC 94.90% AT 215 MS = 468.3 |
| 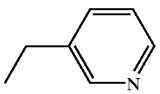 | HPLC 100% AT 215 MS = 377.2 |
| 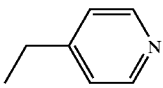 | HPLC 100% AT 215 MS = 377.2 |
|  | HPLC 90.27% AT 215 MS = 460.3    HPLC QUAT. 95.78% AT 215 MS = 634 |
| 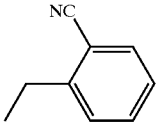 | HPLC 96.6% AT 215 MS = 401.3 |

EXAMPLE 66
Naphthalen-1-ylmethyl-(3-phenylisoxazol-5-yl)-(3-azepan-yl-(2-methyl)-propyl-amine

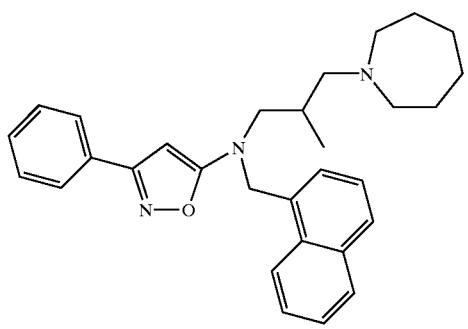

Step 1: Naphthalen-1-ylmethyl-(3-phenyl-isoxazol-5-yl)-((3-chloro-2-methyl)-propyl)amine To a solution of naphthalen-1-ylmethyl-(3-phenyl-isoxazol-5-yl)amine(576 mg, 0.002 m) in DMF (5 ml) under argon was added sodium hydride(76 mg, 60% in oil). The reaction miture turned yellow and foamed. After 5 minutes, 1-bromo-3-chloro-2-methyl propane(342 mg, 0.002 m) was added. After stirring overnight, the DMF was removed under reduced pressure. The gum was dissolved in ethyl acetate and washed with sodium bicarbonate, water, brine and dried over sodium sulfate. Filtered and concentrated to yield an oil, which was purified by a flash 8"×50 mm silica column using 20% ethyl acetate/hexane as solvent, was isolated as the bottom spot and 103 mg(13.1% was obtained as a semi solid. HPLC 99.57% at 215; 100% at 254. NMR consistent with structure.

Step 2: Naphthalen-1-ylmethyl-(phenylisoxazol-5-yl)-(3-azepin-(2-methyl)-propyl)amine To a solution of naphthalen-1-ylmethyl-(3-phenyl-isoxazol-5-yl)-((3-chloro-2-methyl)-propyl)amine(43 mg, 0.00011 m) in DMF (0.5 ml) was added hexamethyleneimine(0.012.3 ml, 0.00011 m). After 2 hours, tlc indicated the presence of starting chloride and more amine(0.024 ml) was added. Heat overnight at 60°.

Removed the DMF under reduced pressure and purified the gum by running a 6"×30 mm silica column using methylene chloride(95), methanol(5) and ammonium hydroxide(0.5). "Title" was obtained as a yellow oil 23 mg 46%. HPLC 98.61% at 254; 94.39% at 215. Mass Spectra cal'd. 453.63; found 454.3.

Analysis:

Cal'd. for $C_{30}H_{35}N_3O \cdot 1.05$ Water C, 76.25; H, 7.91; N, 8.89.

Found C, 76.21; H, 7.96; N, 9.11.

EXAMPLE 67

Naphthalen-1-ylmethyl-(phenyl-isoxazol-5-yl)-(3piperidin-yl-(2-methyl)-propyl)amine

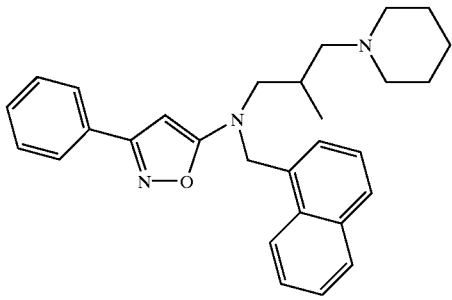

Prepared by the same procedure as EXAMPLE 66 except substituting piperidine in step 2.

HPLC:99.69% at 215; 100% at 254. Mass Spectra cal'd 439.6; found 440.3.

Analysis:

Cal'd for $C_{29}H_{33}H_3O \cdot 0.85$ Water C, 76.56; H,7.69; N, 9.24.

Found: C, 76.56; H, 7.71; N, 9.55.

EXAMPLE 68

Naphthalene-1-ylmethyl(2-azepan-1-yl-propyl)-(3-phenyl-isoxazol-5-yl)-amine

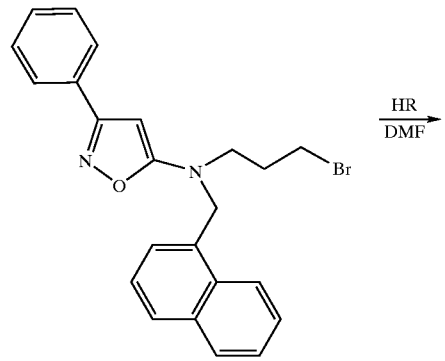

-continued

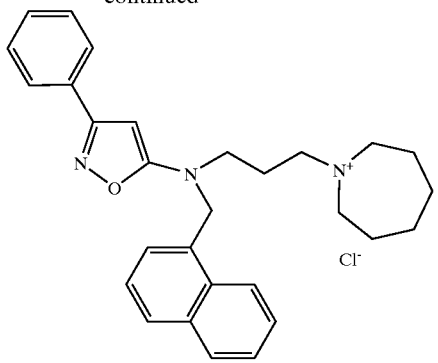

Step 1: 2-naphthalen-1-ylmethyl-(3-phenyl-1soxazol-5-yl)-1-bromopropane

Prepared in a manner similar to that described above from naphthalen-1-ymethyl-(3-phenyl-isoxazol-5-yl)amine Step 2: Prep. of (2-azepan-1-yl-propyl)-naphthalene-1-ylmethyl-(3-phenyl-isoxazol-5-yl)-amine To a solution of 2-naphthalen-1-ylmethyl-(3-phenyl-lsoxazol-5-yl)-1-bromopropane(96 mg of a 65%–35% bromo to olefin, 0.000159 m) in DMF(3 ml) was added hexamethylimine(0.037 ml). After stirring for 1 hour, the reaction was not complete by tlc. An additional 0.028 ml of amine was added. After 1 hour, the reaction was complete. Removed the DMF under reduced pressure and purified the product by column chromatography using a 50 mm×6" flash silica column with methylene chloride(940 ml), methanol (54 ml), and ammonium hydroxide(6 ml) as solvent. Collect the product fractions and concentrate to an oil. Dissolve the oil in ethanol and add 0.800 ml of 1M HCl in ether. Remove the solvents under reduced pressure. Add hexan/ether and remove 4 times. Add ether, scratch and filter to give 49 mg(70%) of the product as a yellow solid. HPLC 97.87% at 215. Mass Spectra cal'd. 439.604: Found 440.27.

Analysis: Calcd. for $C_{29}H_{33}N_3O \cdot HCl \cdot 0.35H_2O + 0.10$ $C_4H_{10}O$ C, 72.09; H, 7.35; N, 8.58.

Found: C, 72.12; H, 6.96; N, 8.41.

EXAMPLE 69

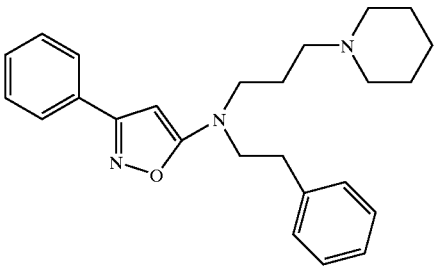

2-phenyl-1-ethyl-(3-phenyl-isoxazol-5-yl)-(3-piperidin-1-yl-propyl)-amine

Step 1: 3-Phenyl-isoxazol-5-yl-(2-phenyl-ethyl)-amine(J)

Phenethyl amine(0.501 ml, 0.004 m) was added to 3-phenyl-5-chloroisoxazole(A) (358 mg, 0.002 m). The solution was heated at 70° for 48 hours. Dissolved the gum in ethyl acetate and washed with sat. aq. sodium bicarbonate. Dried the organics with sodium sulfate, filtered, and concentrated to an oil. Purified the oil by "flash" chromatograph using 6"×50 mm silica with methylene chloride(95), methanol(5), and ammonium hydroxide(0.5) as solvent. HPLC; 86.02% at 210. NMR $^1$H (CDCl$_3$)7.79–7.76(m, 2H), 7.42–7.4(m, 3H), 7.38–7.28(m, 2H), 7.6–7.2(m, 3H), 5.4(s, 1H), 4.6–4.6(t, 1H), 3.6–3.46(q, 2H), 3.0–2.92(t, 2H).

Step 2: 2-Phenyl-1-ethyl-(3-phenyl-isoxazol-5-yl)-(3-bromo-1-yl-propyl)-amine

To a solution of 3-phenyl-isoxazol-5-yl-(2-phenyl-ethyl)-amine (156 mg, 0.00059 m) in DMF(3 ml) under argon was added sodium hydride(58 mg, 0.0024 m). The reaction foamed and turned yellow. After 5 minutes, 1,3-dibromopropane(0.239.52 ml) was added. After 2 hours the reaction was complete. Removed the DMF under reduced pressure. The gum was dissolved in ethyl acetate and wae washed with sodium bicarbonate(sat. aq.), water and brine. The ethyl acetate was dried over sodium sulfate, filtered and concentrated to an oil. The olefin and bromide formed in the reaction were purified by a 50 mm×6" silica flash column using 10% ethyl acetate/hexane as solvent. NMR $^1$H (CDCl$_3$) 7.69–7.66(m, 2H), 7.46–7.4(m, 3H) 7.34–7.28(m, 2H), 7.28–7.20(m, 3H), 5.35(s, 1H), 3.65–3.59(t, 2H), 3.47–3.39(m, 4H), 3.02–2.85(t, 2H), 2.2–2.1(m, 2H).

Step 3: 2-Phenyl-1-ethyl-(3-phenyl-isoxazol-5-yl)-(3-piperidin-1-yl-propyl)-amine To a solution of 2-Phenyl-1-ethyl-(3-phenyl-isoxazol-5-yl)-(3-bromo-1-yl-propyl)-amine(K)(58.9 mg, 00015 m) in DMF (1 ml) was added piperidine(0.1 ml, x's.) After 1 hour, the DMF was removed under reduced pressure. The gum was dissolved in ethyl acetate and washed with sodium bicarbonate (sat. aq.), water, and brine. The organics were dried over sodium sulfate, filtered and concentrated to an oil (22 mg, 37.9%). HPLC 95.95% at 215. Mass Spectra cal'd.=389.54; found 390.3.

Analysis: cal'd for C$_{25}$H$_{31}$N$_3$O.0.4 water C, 75.68; H, 8.08; N, 10.59.

Found: C, 75.71; H, 8.15; N, 10.74.

EXAMPLE 70

Table 4 includes phenethyl amine derivatives made by the same sequence as described above with the use of 1-iodo-3-chloropropane in step A. The final products were purified by 6"×25 mm "flash" silica column chromatography using methylenelchloride(95), methanol(5), and ammonium hydroxide(0.5) as solvent. They were characterized by NMR, Mass Spectra, HPLC and C,H,N analysis.

TABLE 4

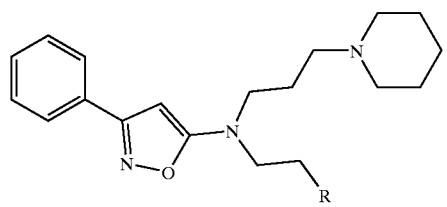

| R = | |
|---|---|
| 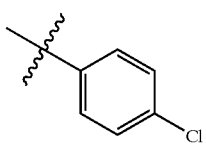 | HPLC:<br>92.35% at 210<br>99.81 at 254<br>Mass Spectra = 424.3 |
| 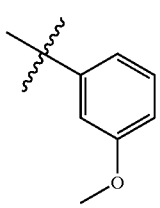 | HPLC:<br>85.68% AT 210<br>98.85% AT 254<br>Mass Spectra = 420.2 |
| 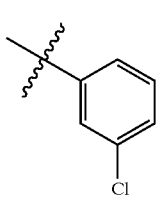 | HPLC:<br>91.92% at 210<br>95.83% at 254<br>Mass Spectra = 424.3 |
| 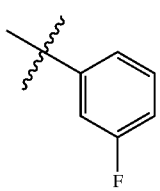 | HPLC:<br>95.39% AT 210<br>96.55% AT 254<br>Mass Spectra = 408.2 |

EXAMPLE 71

Naphthalen-1-ylmethyl-(3-phenyl-isoxazol-5-yl)-(2-piperidin-1-yl-ethyl)-amine Hydrochloride

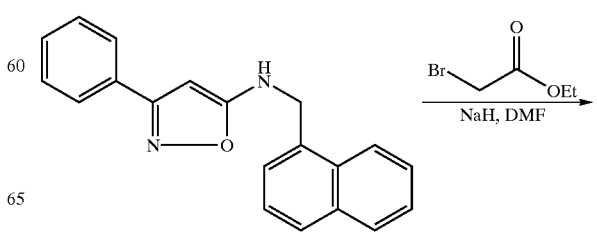

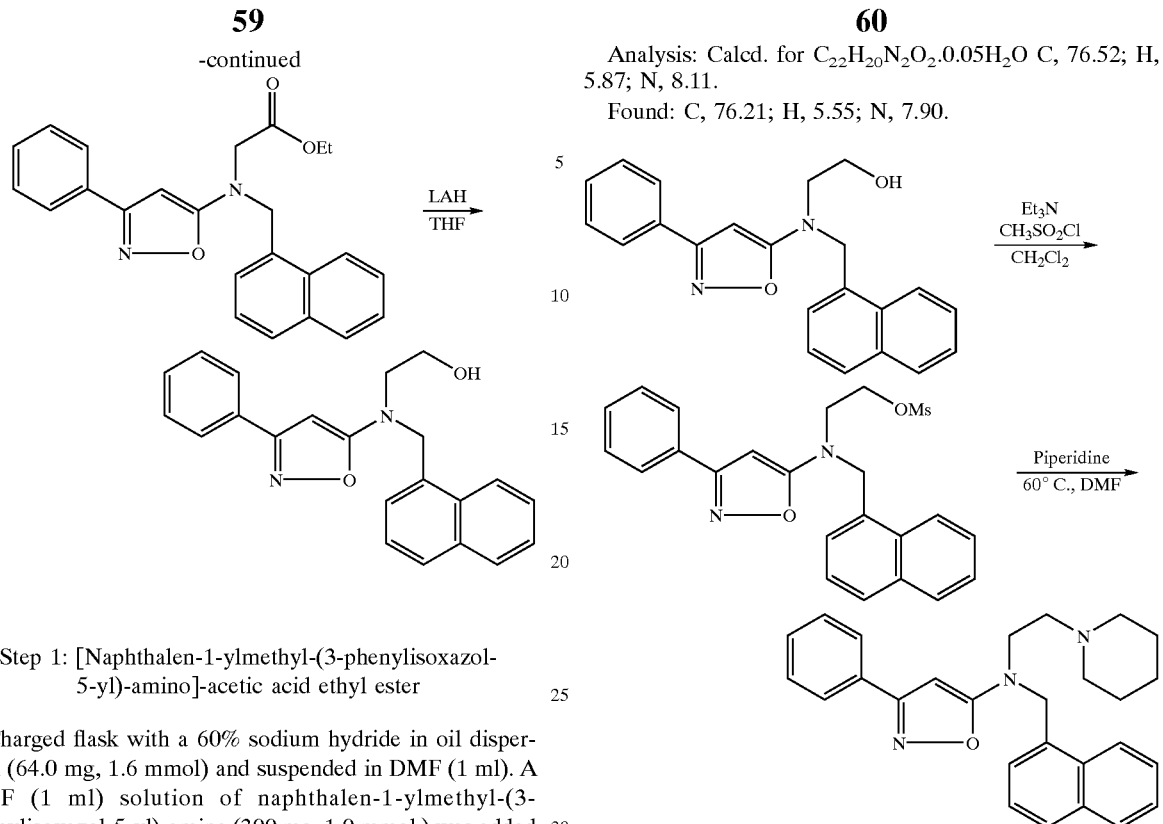

Step 1: [Naphthalen-1-ylmethyl-(3-phenylisoxazol-5-yl)-amino]-acetic acid ethyl ester Charged flask with a 60% sodium hydride in oil dispersion (64.0 mg, 1.6 mmol) and suspended in DMF (1 ml). A DMF (1 ml) solution of naphthalen-1-ylmethyl-(3-phenylisoxazol-5-yl)-amine (300 mg, 1.0 mmol) was added and the mixture stirred under argon at rt for 30 min resulting in a light yellow solution. After adding ethyl bromoacetate (333 µl, 3.0 mmol), the reaction was stirred at rt for 1 hr, poured into 10% sodium bicarbonate (aq) and extracted with ethyl acetate (3×). The extracts were combined, washed with brine, dried over magnesium sulfate, filtered and concentrated in vacuo to give a crude oil (370 mg). Flash chromatography on silica gel (15% ethyl acetate in hexane) gave the title compound as a colorless oil (306 mg, 73.9%).

$^1$H NMR (CDCl$_3$): δ8.02–7.97 (m, 1H), 7.94–7.85 (m, 2H), 7.80–7.76 (m, 2H), 7.57–7.52 (m, 2H), 7.47–7.41 (m, 5H), 5.46 (s, 1H), 5.10 (s, 2H), 4.17 (q, 2H, J=24 Hz), 3.93 (s, 2H), 1.24 (t, 3H, J=24 Hz).

Step 2: 2-[Naphthalen-1-ylmethyl-(3-phenylisoxazol-5-yl)-amino]ethanol

[Naphthalen-1-ylmethyl-(3-phenyl-isoxazol-5-yl)-amino]-acetic acid ethyl ester (305 mg, 0.789 mmol) was dissolved in tetrahydrofuran (THF, 2 ml) and while stirring under argon, treated with a 1.0M lithium aluminum hydride in diethyl ether solution (1.58 ml, 1.58 mmol) and stirred at rt for 1.5 hr. The reaction was diluted with THF (2 ml), followed by diethyl ether (10 ml), and water was added slowly dropwise to give a filterable solid. The mixture was filtered through super cel, the filter cake washed well with a THF/diethyl ether (1/4), and the filtrate stripped to dryness in vacuo to give a crude oil (200 mg). Flash chromatography on silica gel (10 to 15% diethyl ether in methylene chloride) gave the product as a white foam (179 mg, 65.9%).

$^1$H NMR (CDCl$_3$): δ7.98–7.87 (m, 2H), 7.86–7.80 (m, 1H), 7.78–7.71 (m, 2H), 7.57–7.52 (m, 2H), 7.47–7.38 (m, 5H), 5.34 (s, 1H), 5.10 (s, 2H), 3.80 (q, 2H, J=18 Hz), 3.56 (t, 2H, J=18 Hz), 1.71 (t, 1H, J=18 Hz).

Analysis: Calcd. for C$_{22}$H$_{20}$N$_2$O$_2$·0.05H$_2$O C, 76.52; H, 5.87; N, 8.11.
Found: C, 76.21; H, 5.55; N, 7.90.

Step 3: Methanesulfonic acid 2-[naphthalen-1-ylmethyl-(3phenylisoxazol-5-yl)-amino]ethyl ester 2-[Naphthalen-1-ylmethyl-(3-phenylisoxazol-5-yl)amino]ethanol (820 mg, 2.38 mmol) was dissolved in methylene chloride (15 ml), treated with triethylamine (592 µl, 4.25 mmol) followed by methanesulfonyl-chloride (265 µl, 3.42 mnmol) and the solution stirred at rt for 1.5 hr. The reaction was washed with 50% sodium bicarbonate (aq, 2×), water (1×), and brine (1×), dried over sodium sulfate, filtered and stripped to dryness in vacuo to give the product as a sticky, foam (1.07 gm, quantitative).

$^1$H NMR (CDCl$_3$): δ7.98–7.90 (m, 2H), 7.89–7.84 (m, 1H), 7.78–7.73 (m, 2H), 7.58–7.52 (m, 2H), 7.47–7.40 (m, 5H), 5.42 (s, 1H), 5.08 (s, 2H), 4.31 (t, 2H, J=18 Hz), 3.71 (t, 2H, J=18 Hz), 2.85 (s, 3H).

Step 4: Naphthalen-1-ylmethyl-(3-phenisoxazol-5-yl)-(2-piperidin-1-yl-ethyl-amine Hydrochloride Piperidine (68.2 µl, 0.689 mmol) and methanesulfonic acid 2-[naphthalen-1-ylmethyl-(3phenyl-isoxazol-5-yl)-amino]-ethyl ester (72.8 mg, 0.172 mmol) were dissloved in DMF (1 ml) and warmed to 60° C. for 18 hr. The reaction was poured into saturated sodium bicarbonate (aq), and extracted with ethyl acetate (3×). The extracts were combined, washed with brine, dried over sodium sulfate, filtered and concentrated in vacuo to give a crude oil (46 mg). Flash chromatography on silica gel (266/10/1 of methylene chloride/methanol/conc. ammonium hydroxide) gave the free base of the title compound as a colorless oil (28 mg, 39.4%).

$^1$H NMR (CDCl$_3$): δ8.02–7.96 (m, 1H), 7.93–7.87 (m, 1 H), 7.85–7.79 (m, 1H), 7.78–7.72 (m, 2H), 7.58–7.49 (m, 2H), 7.48–7.37 (m, 5H), 5.28.(s, 1H), 5.07 (s, 2H), 3.48 (t, 2H, J=24 Hz), 2.51 (t, 2H, J=24 Hz), 2.38–2.28 (m, 4H), 1.56–1.47 (m, 4H), 1.45–1.34(m, 2H).

The hydrochloride salt was prepared from ethyl acetate/ether with 1N hydrochloric acid in ether (25.7 mg, 33.3%).

Analysis: Calcd: for $C_{27}H_{29}N_3O \cdot HCl \cdot 0.45H_2O \cdot 0.30C_4H_8O_2$ C, 70.19; H, 6.96; N, 8.71.

Found: C, 70.21; H, 6.97; N, 8.32.

EXAMPLE 72

Naphthalen-1-ylmethyl-(2-Azepan-1-yl-ethyl)-(3-phenyl-isoxazol-5-yl)-amine Hydrochloride

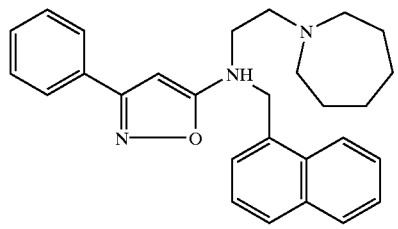

(2-Azepan-1-yl-ethyl)-naphthalen-1-ylmethyl-(3-phenyl-isoxazol-5-yl)-amine Hydrochloride was prepared using the method described above. Azepine (76.4 μl, 0.678 mmol) was used in place of piperidine and the HCl salt was obtained (29.5 mg, 37.7%).

Analysis: Calcd. for $C_{28}H_{31}N_3O \cdot HCl \cdot 0.55H_2O \cdot 0.10C_4H_8O_2$ C, 70.95; H, 7.11; N, 8.74.

Found: C, 70.94; H, 6.86; N, 8.40.

EXAMPLE 73

Table 5 below contains examples prepared in a manner similar to that described for Example 71

TABLE 5

| Structure | HPLC: | | Mass Spectra | |
|---|---|---|---|---|
| cyclopropylmethyl-N-propyl | 210 | 99.77% | CAL'D. | 440.27 |
|  | 254 | 99.92% | FOUND | 440.27 |
| isopropyl-N-methyl | 210 | 95.01% | CAL'D. | 400.24 |
|  | 254 | 95.89% | FOUND | 400.24 |
| HN-diisopropyl | 210 | 95.44% | CAL'D. | 442.29 |
|  | 254 | 97.82% | FOUND | 442.29 |
| furfuryl-HN | 210 | 99.41% | CAL'D. | 424.202 |
|  | 254 | 99.75% | FOUND | 424.20 |

TABLE 5-continued

| Structure | HPLC: | | Mass Spectra | |
|---|---|---|---|---|
| tetrahydronaphthalen-1-yl-NH | 210 | 99.96% | CAL'D. | 474.254 |
|  | 254 | 98.85% | FOUND | 474.26 |
| HN-allyl | 210 | 99.51% | CAL'D. | 383.496 |
|  | 254 | 99.70% | FOUND | 384.26 |
| HN-CH2-(4-methoxyphenyl) | 210 | 99.26% | CAL'D. | 464.233 |
|  | 254 | 98.12% | FOUND | 464.24 |
| HN-sec-butyl | 210 | 98.82% | CAL'D. | 414.254 |
|  | 254 | 98.23% | FOUND | 414.26 |
| piperazinyl-(2-cyanophenyl) | 210 | 99.98% | CAL'D. | 514.26 |
|  | 254 | 99.96% | FOUND | 514.27 |
| HN-cyclopentyl | 210 | 99.99% | CAL'D. | 411.55 |
|  | 254 | 99.31% | FOUND | 412.24 |
| HN-isohexyl | 210 | 99.37% | CAL'D. | 428.27 |
|  | 254 | 99.94% | FOUND | 428.27 |
| HN-CH(Et)-CH2OH | 210 | 99.92% | CAL'D. | 416.233 |
|  | 254 | 99.53% | FOUND | 416.24 |
| HN-cyclobutyl | 210 | 99.21% | CAL'D. | 398.223 |
|  | 254 | 99.71% | FOUND | 398.22 |
| piperidinyl-dioxolane spiro | 210 | 99.98% | CAL'D. | 470.24 |
|  | 254 | 100% | FOUND | 470.24 |

TABLE 5-continued

| | HPLC: | | Mass Spectra | |
|---|---|---|---|---|
| sec-butylamino | 210 | 97.18% | CAL'D. | 400.238 |
| | 254 | 96.19% | FOUND | 400.25 |
| 4-methylpiperazinyl | 210 | 99.43% | CAL'D. | 427.24 |
| | 254 | 99.46% | FOUND | 427.25 |
| ethyl isonipecotate | 210 | 99.93% | CAL'D. | 484.259 |
| | 254 | 100% | FOUND | 484.26 |
| (1-methyl-2-pyrrolidinyl)methylamino | 210 | 99.71% | CAL'D. | 454.619 |
| | 254 | 85.84% | FOUND | 455.28 |
| pyrrolidinyl | 210 | 99.87 | CAL'D. | 398.22 |
| | 254 | 99.87 | FOUND | 398.22 |
| cyclopropylmethylamino | 210 | 99.97% | CAL'D. | 397.52 |
| | 254 | 99.69% | FOUND | 398.22 |
| cyclohexylamino | 210 | 99.92% | CAL'D. | 425.57 |
| | 254 | 99.54% | FOUND | 426.25 |

EXAMPLE 74

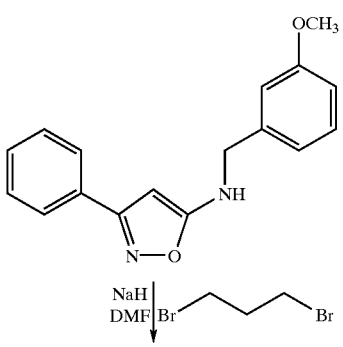

Table 6 below contain 43 examples of products obtained by the general reaction schemeabove, purity (HPLC) and mass spec (FAB) is given for each example.

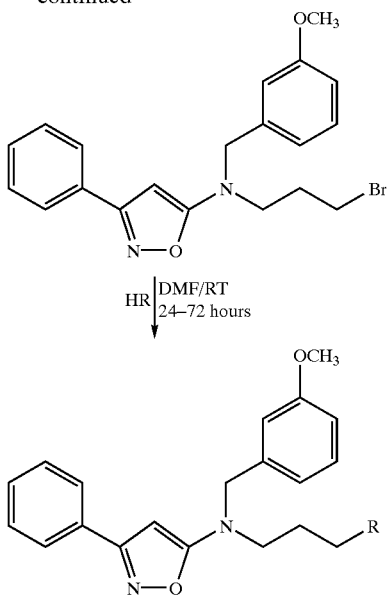

TABLE 6

| R | |
|---|---|
| HN-ethyl | HPLC: 98.7% at 254<br>MS: M + H = 366.1 |
| HN-propyl | HPLC: 99.2% at 254<br>MS: M + H = 380.1 |
| HN-butyl | HPLC: 99.6% at 254<br>MS: M + H = 394.2 |
| HN-pentyl | HPLC: 98.5% at 254<br>MS: M + H = 408.2 |
| HN-isobutyl | HPLC: 99.1% at 254<br>MS: M + H = 394.2 |
| HN-neopentyl | HPLC: 99.2% at 254<br>MS: M + H = 408.2 |
| HN-cyclohexylmethyl | HPLC: 93.6% at 254<br>MS: M + H = 434.2 |
| HN-(2,4-dimethyl-3-pentyl) | HPLC: 100% at 254<br>MS: M + H = 436.2 |
| HN-(1-adamantylmethyl) | HPLC: 97.9% at 254<br>MS: M + H = 486.2 |

TABLE 6-continued

| R | | |
|---|---|---|
| (CH3CH2)2N-CH2CH2- structure | HPLC: 96.6% at 254 | MS: M + H = 422.2 |
| HN-CH(Et)2 | HPLC: 98.8% at 254 | MS: M + H = 408.2 |
| azocane (N-8-ring) | HPLC: 99.2% at 254 | MS: M + H = 434.2 |
| N(CH2-cPr)(n-Pr) | HPLC: 98.8% at 254 | MS: M + H = 434.2 |
| N(Me)(iBu) | HPLC: 99.5% at 254 | MS: M + H = 394.1 |
| azepane | HPLC: 100% at 254 | MS: M + H = 420.3 |
| HN-tBu | HPLC: 100% at 254 | MS: M + H = 394.2 |
| HN-CH2Ph | HPLC: 100% at 254 | MS: M + H = 428.2 |
| N-methylpiperazine | HPLC: 100% at 254 | MS: M + H = 421.3 |
| N-benzylpiperazine | HPLC: 100% at 254 | MS: M + H = 497.3 |
| 1,4-dioxa-8-azaspiro[4.5]decane | HPLC: 100% at 254 | MS: M + H = 464.2 |
| 1,2,3,4-tetrahydroisoquinoline | HPLC: 100% at 254 | MS: M + H = 454.3 |
| HN-CH(CH3)Ph | HPLC: 100% at 254 | MS: M + H = 442.3 |
| N-methylhomopiperazine | HPLC: 100% at 254 | MS: M + H = 435.2 |
| ethyl piperidine-2-carboxylate | HPLC: 100% at 254 | MS: M + H = 464.2 |
| thiazolidine | HPLC: 78.0% at 254 | MS: M + H = 410.2 |
| 1-(2-pyridyl)piperazine | HPLC: 100% at 254 | MS: M + H = 484.3 |
| ethyl piperidine-4-carboxylate | HPLC: 100% at 254 | MS: M + H = 478.3 |
| H2N-CH2-CH=CH2 | HPLC: 100% at 254 | MS: M + H = 378.2 |
| H2N-cyclohexyl | HPLC: 100% at 254 | MS: M + H = 420.3 |
| H2N-CH2CH2-(1-methylpyrrolidin-2-yl) | HPLC: 100% at 254 | MS: M + H = 449.3 |
| H3CHN-cyclohexyl | HPLC: 100% at 254 | MS: M + H = 434.3 |
| 4-amino-1-benzylpiperidine | HPLC: 90.1% at 254 | MS: M + H = 511.3 |
| pyrrolidine | HPLC: 100% at 254 | MS: M + H = 392.3 |
| H2N-iPr | HPLC: 100% at 254 | MS: M + H = 380.2 |
| spiro[indene-1,4'-piperidine] | HPLC: 100% at 254 | MS: M + H = 506.3 |

TABLE 6-continued

| R | |
|---|---|
| HN-CH2-cyclopropyl | HPLC: 100% at 254<br>MS: M + H = 392.2 |
| HN-adamantyl | HPLC: 95.2% at 254<br>MS: M + H = 472.3 |
| piperidinyl-benzimidazolone | HPLC: 100% at 254<br>MS: M + H = 538.3 |
| 4,4'-bipiperidine | HPLC: 100% at 254<br>MS: M + H = 489.3 |
| 3-carbamoyl-piperidinyl (CONH2) | HPLC: 100% at 254<br>MS: M + H = 449.3 |
| N(CH3)CH2CN | HPLC: 91.4% at 254<br>MS: M + H = 391.2 |
| HN-CH2-CO2Et | HPLC: 94.0% at 254<br>MS: M + H = 424.2 |
| azetidinyl | HPLC: 100% at 254<br>MS: M + H = 378.2 |

EXAMPLE 75

Naphthalen-1-ylmethyl-(3-phenyl-isoxazol-5-yl)-(4-piperidin-1-yl-butyl)-amine Hydrochloride

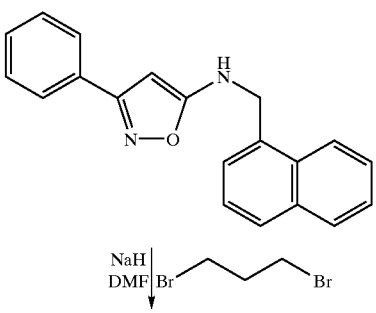

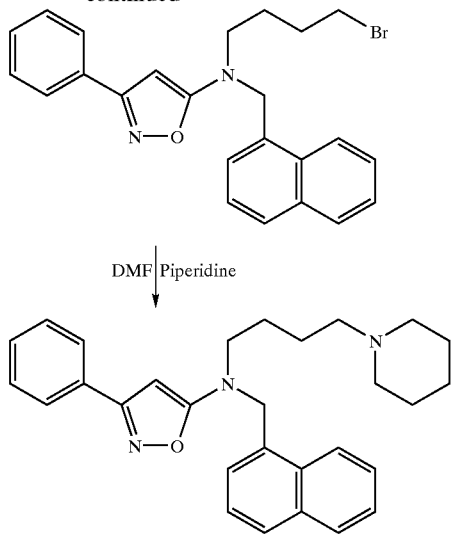

Step 1: (4-bromo-butyl)-naphthalen-1-ylmethyl-(3-phenyl-isoxazol-5-yl)-amine

Charged flask with a 60% sodium hydride in oil dispersion (64.0 mg, 1.6 mmol) and suspended in DMF (1 ml). A DMF (1 ml) solution of naphthalen-1-ylmethyl-(3-phenyl-isoxazol-5-yl)-amine (300 mg, 1.0 mmol) was added and the mixture stirred under argon at rt for 30 min resulting in a light yellow solution. After adding 1,4-dibromobutane (358 μl, 3.0 mmol), the reaction was stirred at rt for 1 hr, poured into 10% sodium bicarbonate (aq) and extracted with ethyl acetate (3x). The extracts were combined, washed with brine, dried over magnesium sulfate, filtered and concentrated in vacuo to give a crude oil (181 mg). Flash chromatography on silica gel (10% ethyl acetate in hexane) gave the product as a colorless oil (114 mg, 26.2%).

$^1$H NMR (CDCl$_3$): δ8.01–7.95 (m, 1H), 7.94–7.88 (m, 1H), 7.86–7.81 (m, 1H), 7.78–7.72 (m, 2H), 7.59–7.50 (m, 2H), 7.48–7.38 (m, 5H), 5.31 (s, 1H), 5.01 (s, 2H), 3.40–3.29 (m, 4H), 1.87–1.70 (m, 4H).

Step 2: Naphthalen-1-ylmethyl-(3-phenylisoxazol-5-yl)-(4-piperidin-1-yl-butyl)amine Hydrochloride)

Piperidine (37.5 ul, 0.378 mmol) and (4-bromobutyl)-naphthalen-1-ylmethyl-(3-phenylisoxazol-5-yl)-amine (55.0 mg, 0.126 mmol) were combined in DMF (1 ml) and stirred at rt for 18 hr. The reaction was poured into saturated sodium bicarbonate (aq), and extracted with ethyl acetate (3x). The extracts were combined, washed with brine, dried over magnesium sulfate, filtered and concentrated in vacuo to give a crude oil (40 mg). Flash chromatography on silica gel (160/10/1 of methylene chloride/methanol/conc. ammonium hydroxide) gave the free base of the product as a colorless oil (40 mg, 72.2%).

$^1$H NMR (CDCl$_3$): δ8.02–7.96 (m, 1H), 7.93–7.88 (m, 1H), 7.85–7.80 (m, 1H), 7.78–7.72 (m, 2H), 7.58–7.49 (m, 2H), 7.46–7.38 (m, 5H), 5.27 (s, 1H), 5.00 (s, 2H), 3.36–3.31 (m, 2H), 2.31–2.21 (m, 6H), 1.67–1.52 (m, 6H), 1.49–1.37 (m, 4H).

The hydrochloride salt was prepared from ethyl acetate/ether with 1N hydrochloric acid in ether (43 mg, 71.7%).

Analysis: Calcd. for $C_{29}H_{33}N_3O \cdot HCl \cdot 0.90H_2O \cdot 0.10C_4H_{10}O$ C, 70.66; H, 7.42; N, 8.41.

Found: C, 70.59; H, 7.35; N, 8.03.

EXAMPLE 76

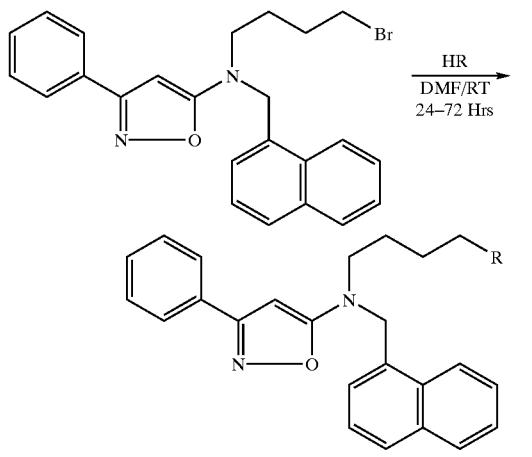

The table 7 below contain 49 examples of products obtained by the general reaction above. A purity (HPLC) and mass spec (FAB) is given for each example.

TABLE 7

| R | |
|---|---|
| N-thiazolidine | HPLC: 85.7% at 254<br>MS: M + H = 444.21 |
| N-piperazinyl-2-pyridine | HPLC: 93.3% at 254<br>MS: M + H = 518.29 |
| N-piperidinyl-CO₂Et | HPLC: 96.0% at 254<br>MS: M + H = 512.3 |
| HN-allyl | HPLC: 94.4% at 254<br>MS: M + H = 412.24 |
| HN-cyclohexyl | HPLC: 89.0% at 254<br>MS: M + H = 454.29 |
| HN-CH₂-(1-methylpyrrolidin-2-yl) | HPLC: 97.9% at 254<br>MS: M + H = 483.31 |
| N(CH₃)-cyclohexyl | HPLC: 88.2% at 254<br>MS: M + H = 468.30 |

TABLE 7-continued

| R | |
|---|---|
| HN-(1-benzylpiperidin-4-yl) | HPLC: 97.4% at 254<br>MS: M + H = 545.33 |
| N-pyrrolidinyl | HPLC: 97.8% at 254<br>MS: M + H = 426.25 |
| HN-isopropyl | HPLC: 87.5% at 254<br>MS: M + H = 414.25 |
| HN-CH₂-cyclopropyl | HPLC: 90.3% at 254<br>MS: M + H = 426.25 |
| N-azetidinyl | HPLC: 98.8% at 254<br>MS: M + H = 412.24 |
| HN-adamantyl | HPLC: 89.8% at 254<br>MS: M + H = 506.32 |
| N-(3-(2-oxo-benzimidazol-1-yl))piperidinyl | HPLC: 94.6% at 254<br>MS: M + H = 572.30 |
| N-(4-piperidinyl)piperidine | HPLC: 97.0% at 254<br>MS: M + H = 523.35 |
| N-piperidinyl-3-CONH₂ | HPLC: 97.7% at 254<br>MS: M + H = 483.28 |
| HN-tert-butyl | HPLC: 76.0% at 254<br>MS: M + H = 428.27 |
| HN-benzyl | HPLC: 90.9% at 254<br>MS: M + H = 462.26 |
| N-(4-methyl)piperazinyl | HPLC: 97.3% at 254<br>MS: M + H = 455.28 |
| N-(4-benzyl)piperazinyl | HPLC: 98.0% at 254<br>MS: M + H = 531.33 |

TABLE 7-continued

| R | | |
|---|---|---|
|  | | HPLC: 97.3% at 254<br>MS: M + H = 498.28 |
|  | | HPLC: 95.2% at 254<br>MS: M + H = 488.28 |
| 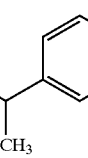 | RS | HPLC: 94.6% at 254<br>MS: M + H = 476.26 |
|  | | HPLC: 97.7% at 254<br>MS: M + H = 469.30 |
|  | | HPLC: 93.8% at 254<br>MS: M + H = 414.25 |
|  | | HPLC: 96.4% at 254<br>MS: M + H = 428.27 |
|  | | HPLC: 88.9% at 254<br>MS: M + H = 442.28 |
|  | | HPLC: 96.2% at 254<br>MS: M + H = 428.27 |
|  | | HPLC: 95.3% at 254<br>MS: M + H = 442.29 |
|  | | HPLC: 94.7% at 254<br>MS: M + H = 468.30 |
|  | | HPLC: 96.4% at 254<br>MS: M + H = 520.34 |
|  | | HPLC: 91.8% at 254<br>MS: M + H = 456.30 |
|  | | HPLC: 89.1% at 254<br>MS: M + H = 442.29 |
|  | | HPLC: 94.5% at 254<br>MS: M + H = 468.30 |

TABLE 7-continued

| R | | |
|---|---|---|
|  | | HPLC: 94.0% at 254<br>MS: M + H = 468.31 |
|  | | HPLC: 84.4% at 254<br>MS: M + H = 428.27 |
|  | | HPLC: 65.1% at 254<br>MS: M + H = 470.32 |
|  | | HPLC: 94.5% at 254<br>MS: M + H = 492.27 |
|  | RS | HPLC: 87.3% at 254<br>MS: M + H = 442.29 |
|  | | HPLC: 96.3% at 254<br>MS: M + H = 542.30 |
|  | | HPLC: 93.4% at 254<br>MS: M + H = 440.27 |
|  | RS | HPLC: 93.5% at 254<br>MS: M + H = 456.31 |
|  | RS | HPLC: 94.5% at 254<br>MS: M + H = 444.27 |
|  | | HPLC: 92.7% at 254<br>MS: M + H = 452.23 |
|  | | HPLC: 93.4% at 254<br>MS: M + H = 430.25 |
|  | | HPLC: 92.3% at 254<br>MS: M + H = 426.26 |
|  | | HPLC: 97.8% at 254<br>MS: M + H = 454.3 |

TABLE 7-continued

| R | | |
|---|---|---|
|  | | HPLC: 94.4% at 254<br>MS: M + H = 502.30 |
|  | S-(+) | HPLC: 82.0% at 254<br>MS: M + H = 428.27 |

Therapeutic Treatment

Compounds of the invention may be administered to patients where inhibition of human or mammalian platelet aggregation or adhesion is desired.

Compounds of the invention are useful in inhibiting platelet aggregation and thus, they may find utility in surgery on peripheral arteries (arterial grafts, carotid endaterectomy) and in cardiovascular surgery where manipulation of arteries and organs, and/or the interation of platelets with artificial surfaces, leads to platelet aggregation and consumption. The aggregated platelets may form thrombi and thromboemboli. Compounds of the invention may be administered to these surgical patients to prevent the formation of thrombi and thromboemboli.

EXAMPLE 77

Tablet Preparation

Tablets containing 25.0, 50.0, and 100.0 mg., respectively, of the active drug 3,4-methylenedioxybenzyl-[3-(3,5-difluorophenyl)-isoxazol-5-yl]-(3-azepin-1-yl-propyl)-amine hydrochloride are prepared as illustrated below:

Table for Doses Containing from 25–100 mg of the Active Compound

| | Amount-mg | | |
|---|---|---|---|
| Active Drug | 25.0 | 50.0 | 100.0 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active drug, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 78

Intravenous Formulations

An intravenous dosage form of active drug 3,4-methylenedioxybenzyl-[3-(3,5-difluorophenyl)-isoxazol-5-yl]-(3-azepin-1-yl-propyl)-amine hydrochloride is prepared as follows:

| Ingredient | Amount |
|---|---|
| Active Drug | 0.5–10.0 mg |
| Sodium Citrate | 5–50 mg |
| Citric Acid | 1–15 mg |
| Sodium Chloride | 1–8 mg |
| Water for Injection (USP) | q.s. to 1 L |

Utilizing the above quantities, the active drug is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md., copyright 1994.

EXAMPLE 79

Intravenous Formulation

A pharmaceutical composition was prepared at room temperature using, a citrate buffer, and sodium chloride, to obtain a concentration of of 0.25 mg/ml.

800 grams of water was introduced into a standard pharmaceutical mixing vessel. 0.25 grams of active drug 3,4-methylenedioxybenzyl-[3-(3,5-difluorophenyl)-isoxazol-5-yl]-(3-azepin-1-yl-propyl)-amine hydrochloride was dissolved in the water. 2.7 grams sodium citrate and 0.16 grams citric acid were added to obtain a finished citrate concentration of 10 mM. 8 grams of sodium chloride was added. 200 grams of water was then added to achieve the desired final concentrations of ingredients. The resulting aqueous formulation had the following concentrations:

| Ingredient | Amount |
|---|---|
| Active drug | 0.25 mg/ml |
| citrate buffer | 10 mM |
| sodium chloride | 8 mg/ml |

The finished concentrated formulation is stored in a standard USP Type I borosilicate glass container at 30–40 degrees C. Prior to compound administration, the concentrated formulation is diluted in a 4:1 ratio resulting in a finished concentration of 0.05 mg/ml and transferred to an infusion bag.

What is claimed is:

1. A compound having the formula

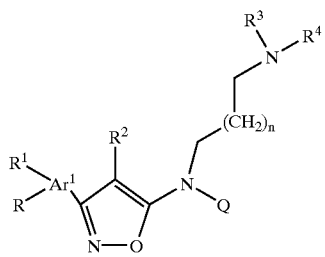

wherein
n is 0, 1, or 2;
m is 0, 1, or 2;

R is
  hydrogen,
  $C_{1-10}$ alkyl,
  $C_{1-10}$ alkoxy,
  aryl,
  halogen,
  $CF_3$,
  $-OCH_3$,
  $SCH_3$,
  $SOCH_3$,
  $SO_2CH_3$,
  $NO_2$,
  CN, or
R, in combination with $R^1$, form a 5-membered heterocyclic ring having 1 or 2 heteroatoms selected from N, O and S;

$R^1$ is
  hydrogen,
  $C_{1-10}$ alkyl,
  $C_{1-10}$ alkoxy,
  aryl,
  halogen,
  $CF_3$,
  $-OCH_3$,
  $SCH_3$,
  $SOCH_3$,
  $SO_2CH_3$,
  $NO_2$,
  CN, or
$R^1$, in combination with R, form a 5-membered heterocyclic ring having 1 or 2 heteroatoms selected from N, O and S;

$R^2$ is
  hydrogen,
  $C_{1-10}$ alkyl,
  $C_{1-10}$ alkoxy,
  halogen, or
  CN;

$R^3$ is
  hydrogen,
  $C_{1-10}$ alkyl,
  $C_{2-10}$ alkenyl,
  $C_{3-10}$ cycloalkyl,
  $CH_2C_{3-10}$ cycloalkyl,
  $(CH_2)_2R^7$,
  $CH_2R^7$,
  CN,
  $CH(CH_3)R^7$,
  $R^7$,

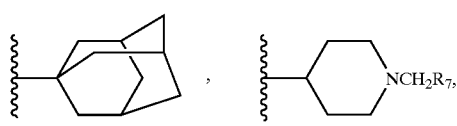, 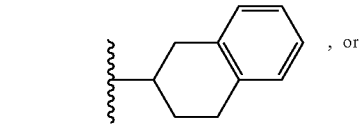, $R^3$, in combination with $R^4$, forms a mono ring system selected from the group consisting of;
  a) a 4–8 membered saturated, partially saturated or unsaturated ring having a nitrogen atom, unsubstituted or substituted with
    1) pyridine,
    2) COOEt,
    3) piperidine,
    4) $CONH_2$,
    5) $C_{1-4}$ alkyl,

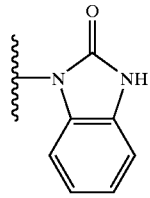 6)

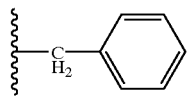 7)

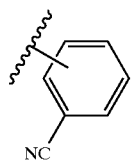 8)

 b)

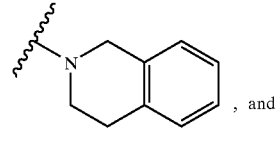, and c)

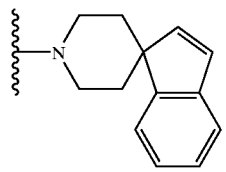 d)

$R^4$ is
  hydrogen,
  $C_{1-10}$ alkyl,
  $C_{2-10}$ alkenyl,
  $C_{3-10}$ cycloalkyl,
  $CH_2C_{3-10}$ cycloalkyl
  $(CH_2)_2R^7$,
  $CH_2R^7$,
  CN,
  $CH(CH_3)R^7$,
  $R^7$, $R^4$, in combination with $R^3$, forms a mono ring system selected from the group consisting of;

a) a 4–8 membered saturated, partially saturated or unsaturated ring having a nitrogen atom, unsubstituted or substituted with
1) pyridine,
2) COOEt,
3) piperidine,
4) CONH$_2$,
5) C$_{1-4}$ alkyl, 6) 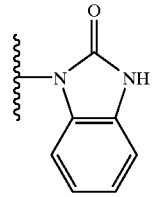

7) 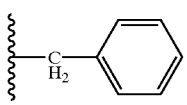

8) 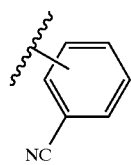

b) 

c) 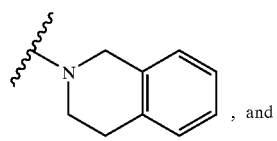, and d) 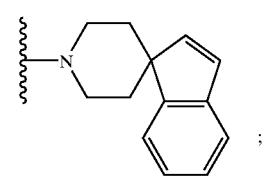;

R$^5$ is
hydrogen,
C$_{1-10}$ alkyl,
C$_{1-10}$ alkoxy,
CN,
OCF$_3$,
—O(CH$_2$)$_{0-2}$R$^8$
—COOCH$_2$CH$_3$, NO$_2$, CF$_3$,
aryl, unsubstituted, monosubstituted or disubstituted with
OCH$_3$,
halogen,
CN,
NO$_2$,
CF$_3$,
OCF$_3$,
OCH$_2$Ph,
OCH$_2$CH$_2$Ph,
COOEt C$_{1-4}$ alkyl, or
phenyl,

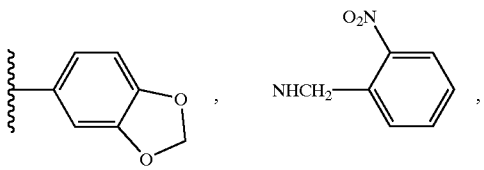

phenyloxy,
halogen, or

R$^5$ and R$^6$ form a 5 membered heterocyclic ring having 1 or 2 heteroatoms selected from N, O and S;

R$^6$ is
hydrogen,
C$_{1-10}$ alkyl,
C$_{1-10}$ alkoxy,
CN,
OCF$_3$,
—O(CH$_2$)$_{0-2}$R$^8$
—COOCH$_2$CH$_3$, NO$_2$, CF$_3$,
aryl, unsubstituted, monosubstituted or disubstituted with
OCH$_3$,
halogen,
CN,
NO$_2$,
CF$_3$,
OCF$_3$,
OCH$_2$Ph,
OCH$_2$CH$_2$Ph,
COOEt,
C$_{1-4}$ alkyl, or
phenyl,

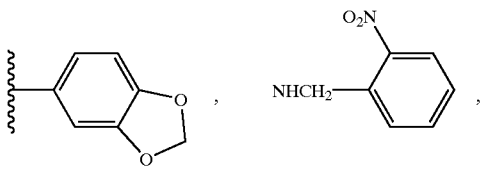

phenyloxy,
halogen, or

R$^6$ and R$^5$ form a 5 membered heterocyclic ring having 1 or 2 heteroatoms selected from N, O and S;

R$^7$ is
phenyl,
CH$_2$OCH$_3$,
C$_{3-6}$ cycloalkyl,

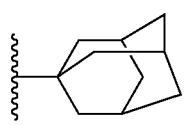 , 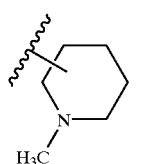 ,

-continued

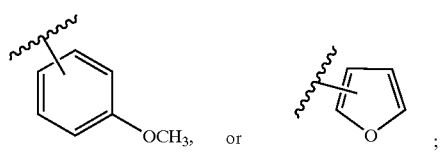

$R^8$ is phenyl; and $Ar^1$ is aryl or heteroaryl;

$Ar^2$ is naphthyl, anthracyl or heteroaryl; and

Q is —$CH_2C_{3-10}$ cycloalkyl, or —$(CH_2)m(Ar^2(R^5)(R^6))$.

2. A compound of claim 1, or a pharmaceutically acceptable salt thereof, wherein $R^2$ is hydrogen.

3. A compound of claim 2, or a pharmaceutically acceptable salt thereof, wherein R is hydrogen, F, Cl, I, $CH_3$, $SCH_3$, $SOCH_3$, $SO_2CH_3$, CN, $NO_2$, or phenyl.

4. A compound of claim 3, or a pharmaceutically acceptable salt thereof, selected from the group consisting of

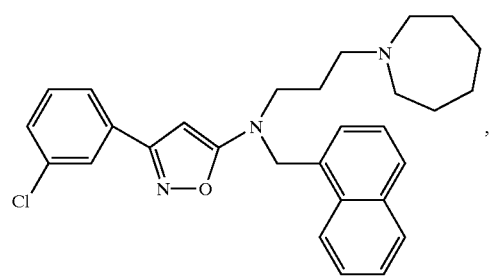

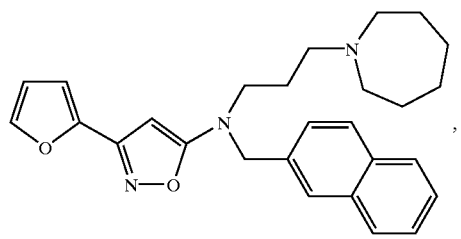

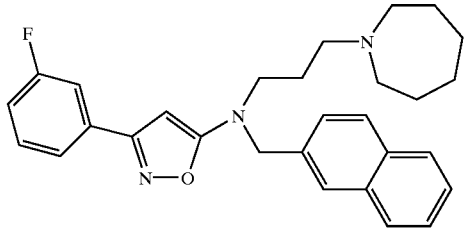

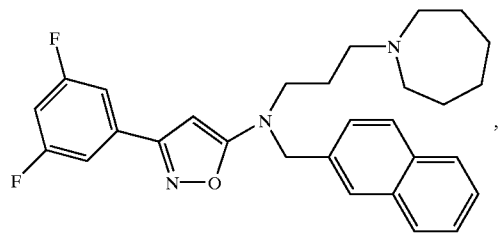

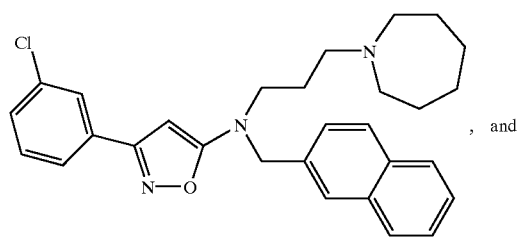

, and

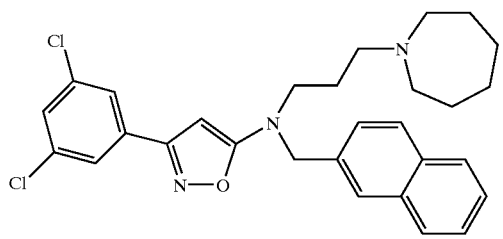

5. A compound or pharmaceutically acceptable salt thereof, selected from the group consisting of

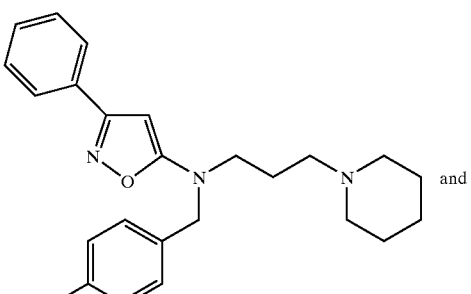

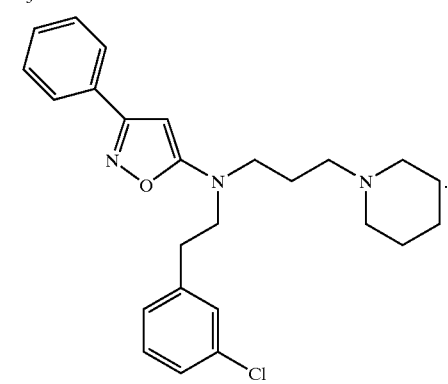

6. A compound selected from the group consisting of

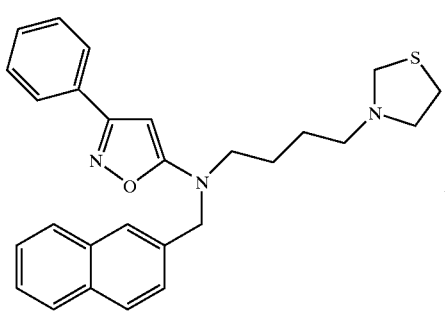

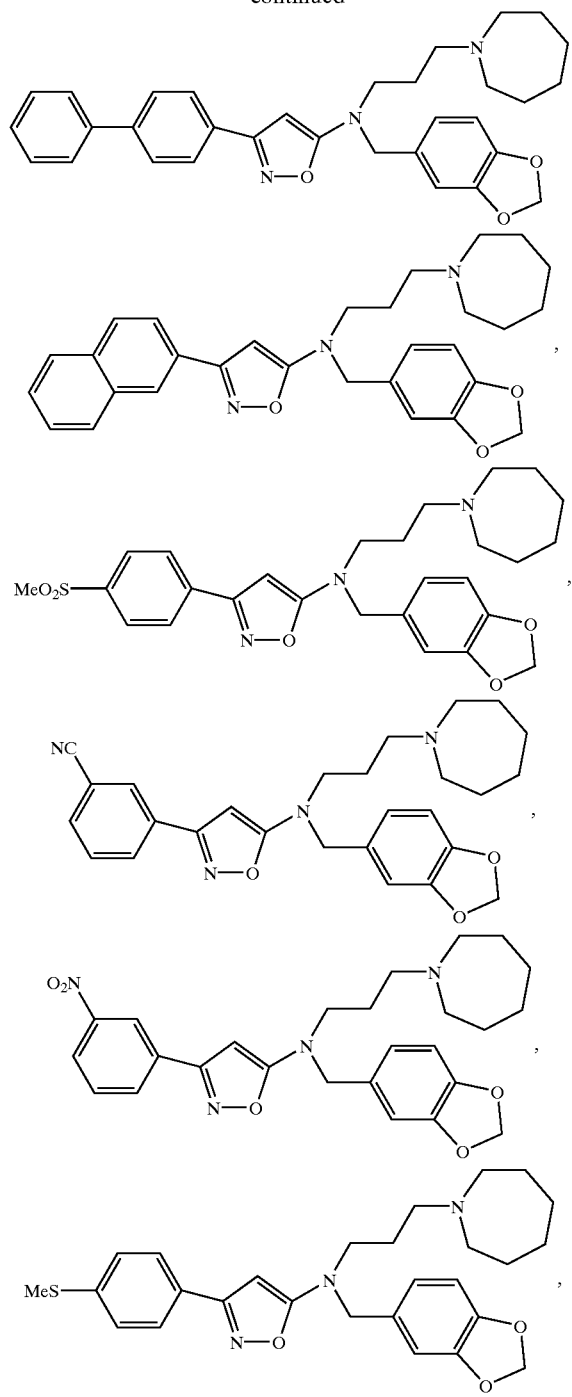
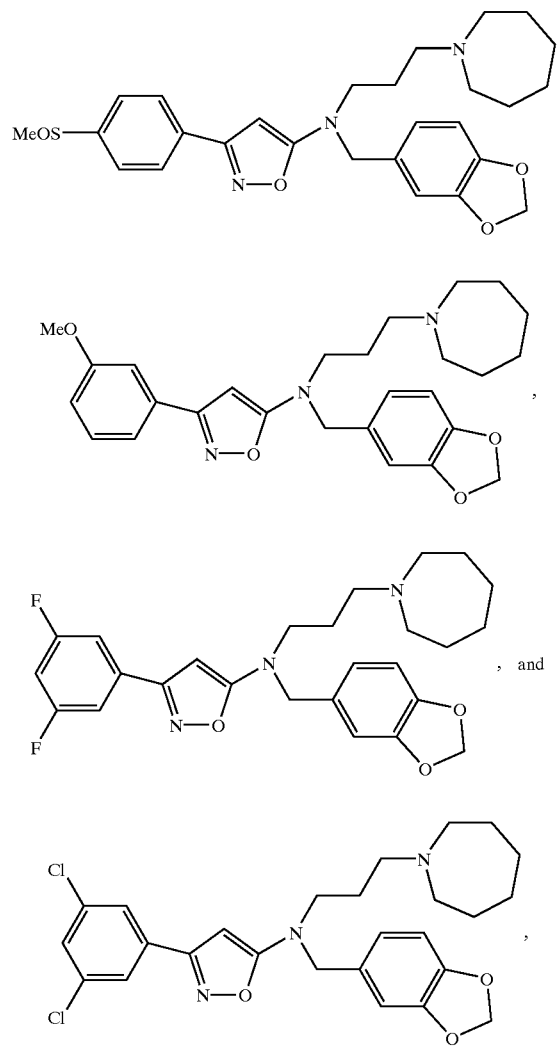
or a pharmaceutically acceptable salt thereof.
7. A pharmaceutical composition comprising a therapeutically effective amount of a compound of claim 1 and a pharmaceutically acceptable carrier.
* * * * *